US012228574B2

(12) United States Patent
Warsinske et al.

(10) Patent No.: US 12,228,574 B2
(45) Date of Patent: Feb. 18, 2025

(54) MARKERS FOR THE EARLY DETECTION OF COLON CELL PROLIFERATIVE DISORDERS

(71) Applicant: Freenome Holdings, Inc., South San Francisco, CA (US)

(72) Inventors: Hayley Warsinske, Daly City, CA (US); Adam Drake, Burlingame, CA (US); Krishnan Kanna Palaniappan, San Francisco, CA (US); Brian D. O'Donovan, San Francisco, CA (US); John Hawkins, San Francisco, CA (US)

(73) Assignee: Freenome Holdings, Inc., San Francisco, CA (US)

( * ) Notice: Subject to any disclaimer, the term of this patent is extended or adjusted under 35 U.S.C. 154(b) by 0 days.

(21) Appl. No.: 18/163,169

(22) Filed: Feb. 1, 2023

(65) Prior Publication Data

US 2023/0176058 A1 Jun. 8, 2023

Related U.S. Application Data

(63) Continuation of application No. PCT/US2021/063337, filed on Dec. 14, 2021.

(60) Provisional application No. 63/128,545, filed on Dec. 21, 2020.

(51) Int. Cl.
*G01N 33/48* (2006.01)
*G01N 33/50* (2006.01)
*G01N 33/574* (2006.01)

(52) U.S. Cl.
CPC ..... *G01N 33/57419* (2013.01); *G01N 2333/52* (2013.01); *G01N 2333/82* (2013.01)

(58) Field of Classification Search
CPC ......... G01N 33/57419; G01N 2333/52; G16B 40/20
See application file for complete search history.

(56) References Cited

U.S. PATENT DOCUMENTS

| | | | |
|---|---|---|---|
| 5,786,146 A | 7/1998 | Herman et al. |
| 7,270,960 B2 | 9/2007 | Hellstrom et al. |
| 7,727,720 B2 | 6/2010 | Dhallan |
| 7,754,429 B2 | 7/2010 | Rigatti et al. |
| 8,168,385 B2 | 5/2012 | Brenner |
| 8,318,433 B2 | 11/2012 | Brenner |
| 8,592,169 B2 | 11/2013 | Robertson et al. |
| 9,040,239 B1 | 5/2015 | Zheng et al. |
| 9,080,210 B2 | 7/2015 | Van Eijk et al. |
| 9,447,452 B2 | 9/2016 | Rao et al. |
| 10,337,053 B2 | 7/2019 | Rao et al. |
| 10,443,091 B2 | 10/2019 | Rao et al. |
| 10,533,213 B2 | 1/2020 | Rao et al. |
| 10,731,204 B2 | 8/2020 | Rao et al. |
| 10,767,216 B2 | 9/2020 | Rao et al. |
| 10,774,373 B2 | 9/2020 | Rao et al. |
| 10,978,175 B2 | 4/2021 | Van Eijk et al. |
| 11,072,818 B2 | 7/2021 | Rao et al. |
| 11,208,683 B2 | 12/2021 | Rao et al. |
| 11,320,436 B2 | 5/2022 | Delfani et al. |
| 11,332,542 B2 | 5/2022 | Berne et al. |
| 11,440,969 B2 | 9/2022 | Lackner et al. |
| 11,447,830 B2 | 9/2022 | Lin et al. |
| 11,514,289 B1 | 11/2022 | Otte et al. |
| 11,621,080 B2 | 4/2023 | Cohen et al. |
| 11,681,953 B2 | 6/2023 | Drake et al. |
| 11,781,959 B2 | 10/2023 | Delubac |
| 11,847,532 B2 | 12/2023 | Drake et al. |
| 2010/0131286 A1 | 5/2010 | Houlgatte et al. |
| 2010/0151471 A1 | 6/2010 | Faham et al. |
| 2012/0143805 A1 | 6/2012 | Gold et al. |
| 2014/0365243 A1 | 12/2014 | Varadan et al. |
| 2016/0069889 A1 | 3/2016 | Spetzler et al. |
| 2016/0238616 A1 | 8/2016 | Masson et al. |
| 2017/0277844 A1 | 9/2017 | Apte et al. |
| 2017/0320950 A1 | 11/2017 | Snyder et al. |
| 2018/0102187 A1 | 4/2018 | Apte et al. |
| 2018/0119137 A1 | 5/2018 | Matsuguchi et al. |
| 2019/0113513 A1 | 4/2019 | Shaked |
| 2019/0178895 A1 | 6/2019 | Lebowitz et al. |
| 2019/0221316 A1 | 7/2019 | Goebel et al. |

(Continued)

FOREIGN PATENT DOCUMENTS

| | | |
|---|---|---|
| EP | 4121770 A1 | 1/2023 |
| EP | 4127724 A1 | 2/2023 |

(Continued)

OTHER PUBLICATIONS

Angelino et al. Discovery of an immunotranscriptomics signature in blood for early colorectal cancer detection. Annals of Oncology, vol. 30, supplement 5, Oct. 2019, abstract 146P.*
Janjua et al. Hyperplastic polyps of the colon and rectum- reclassification, BRAF and KRAS status in index polyps and subsequent colorectal carcinoma. APMIS, vol. 123, pp. 298-304. (Year: 2015).*
Asmus et al.: Simultaneous Targeted Methylation Sequencing (sTM-Seq). Curr Protoc Hum Genet 101(1):e81, pp. 1-19 doi:10.1002/cphg.81 (2019).
Booth et al. Quantitative Sequencing of 5-Methylcytosine and 5-Hydroxymethylcytosine at Single-Base Resolution. Science 336(6083):934-937 (2012).

(Continued)

*Primary Examiner* — Russell S Negin
(74) *Attorney, Agent, or Firm* — Wilson Sonsini Goodrich & Rosati

(57) ABSTRACT

Systems, media, compositions, methods, and kits disclosed herein relate to a panel of protein biomarkers for the early detection of colon cell proliferative disorders, including colorectal cancer. The presence or levels of the proteins in a biological sample for the protein panels described herein may be used for classifier generation, and as inputs in machine learning models useful to classify subjects in a population for the detection of colon cell proliferative disorders.

20 Claims, 5 Drawing Sheets

(56) References Cited

U.S. PATENT DOCUMENTS

| | | |
|---|---|---|
| 2019/0300964 A1 | 10/2019 | Zhang et al. |
| 2019/0376976 A1 | 12/2019 | Killary et al. |
| 2020/0011871 A1 | 1/2020 | Fritsche et al. |
| 2020/0025766 A1 | 1/2020 | Hanash et al. |
| 2020/0033351 A1 | 1/2020 | Levanon et al. |
| 2020/0057070 A1 | 2/2020 | Glezer et al. |
| 2020/0096513 A1 | 3/2020 | Brody et al. |
| 2020/0182878 A1 | 6/2020 | Moore et al. |
| 2020/0209248 A1 | 7/2020 | Lillard et al. |
| 2020/0232894 A1 | 7/2020 | Delubac |
| 2020/0256874 A1 | 8/2020 | Mansfield et al. |
| 2020/0292548 A1 | 9/2020 | Kiebish et al. |
| 2020/0377956 A1 | 12/2020 | Vogelstein et al. |
| 2021/0010076 A1 | 1/2021 | Delubac et al. |
| 2021/0025895 A1 | 1/2021 | Wang et al. |
| 2021/0057046 A1 | 2/2021 | Liu et al. |
| 2021/0072246 A1 | 3/2021 | Henderson et al. |
| 2021/0139999 A1 | 5/2021 | Bromley et al. |
| 2021/0174958 A1 | 6/2021 | Drake et al. |
| 2021/0210205 A1 | 7/2021 | Drake et al. |
| 2021/0215697 A1 | 7/2021 | Holt et al. |
| 2021/0230684 A1 | 7/2021 | Ariazi et al. |
| 2021/0239716 A1 | 8/2021 | Duguez et al. |
| 2021/0254178 A1 | 8/2021 | Willingham et al. |
| 2021/0255189 A1 | 8/2021 | Gyllensten et al. |
| 2021/0255190 A1 | 8/2021 | Willingham et al. |
| 2021/0272653 A1 | 9/2021 | Ulz et al. |
| 2022/0026431 A1 | 1/2022 | Delfani et al. |
| 2022/0049301 A1 | 2/2022 | Violette et al. |
| 2022/0057395 A1 | 2/2022 | Eastman et al. |
| 2022/0120763 A1 | 4/2022 | Villarreal |
| 2022/0128563 A1 | 4/2022 | Pannell et al. |
| 2022/0162705 A1 | 5/2022 | Denkert et al. |
| 2022/0206004 A1 | 6/2022 | Borrebaeck et al. |
| 2022/0214345 A1 | 7/2022 | Schrotz-King et al. |
| 2022/0243278 A1 | 8/2022 | Taylor et al. |
| 2022/0244261 A1 | 8/2022 | Gawel |
| 2022/0276249 A1 | 9/2022 | Martín Rodríguez et al. |
| 2022/0291221 A1 | 9/2022 | Micallef et al. |
| 2022/0317125 A1 | 10/2022 | Gunning et al. |
| 2022/0317126 A1 | 10/2022 | Zhang et al. |
| 2022/0325352 A1 | 10/2022 | Davicioni et al. |
| 2022/0326243 A1 | 10/2022 | Lee et al. |
| 2022/0363760 A1 | 11/2022 | Szabo et al. |
| 2022/0397579 A1 | 12/2022 | Kanjananimmanont et al. |
| 2023/0027606 A1 | 1/2023 | Howell et al. |
| 2023/0063827 A1 | 3/2023 | Speicher et al. |
| 2023/0064677 A1 | 3/2023 | Lackner et al. |
| 2023/0086542 A1 | 3/2023 | Bhardwaj et al. |
| 2023/0203593 A1 | 6/2023 | Scilimati et al. |

FOREIGN PATENT DOCUMENTS

| | | | |
|---|---|---|---|
| WO | WO-2016119190 A1 | 8/2016 | |
| WO | WO-2017004243 A1 | 1/2017 | |
| WO | WO-2019060716 A1 | 3/2019 | |
| WO | WO-2019067092 A1 * | 4/2019 | .......... C12Q 1/6827 |
| WO | WO-2019100024 A1 | 5/2019 | |
| WO | WO-2019147663 A1 | 8/2019 | |
| WO | WO-2019191649 A1 | 10/2019 | |
| WO | WO-2019195268 A2 | 10/2019 | |
| WO | WO-2019200410 A1 | 10/2019 | |
| WO | WO-2020076772 A1 | 4/2020 | |
| WO | WO-2020243609 A1 | 12/2020 | |
| WO | WO-2021013891 A1 | 1/2021 | |
| WO | WO-2021092220 A1 | 5/2021 | |
| WO | WO-2021146659 A1 | 7/2021 | |
| WO | WO-2021188863 A1 | 9/2021 | |
| WO | WO-2021202351 A1 | 10/2021 | |
| WO | WO-2021202959 A1 | 10/2021 | |
| WO | WO-2021222220 A2 | 11/2021 | |
| WO | WO-2021228888 A1 | 11/2021 | |
| WO | WO-2021261483 A1 | 12/2021 | |
| WO | WO-2022015700 A1 | 1/2022 | |
| WO | WO-2022032014 A2 | 2/2022 | |
| WO | WO-2022074645 A1 | 4/2022 | |
| WO | WO-2022076237 A1 | 4/2022 | |
| WO | WO-2022104212 A1 | 5/2022 | |
| WO | WO-2022135552 A1 | 6/2022 | |
| WO | WO-2022140116 A1 | 6/2022 | |
| WO | WO-2022140576 A1 | 6/2022 | |
| WO | WO-2022150447 A1 | 7/2022 | |
| WO | WO-2022189445 A1 | 9/2022 | |
| WO | WO-2022204358 A1 | 9/2022 | |
| WO | WO-2022255401 A1 | 12/2022 | |
| WO | WO-2022261192 A1 | 12/2022 | |
| WO | WO-2023003851 A1 | 1/2023 | |
| WO | WO-2023004078 A2 | 1/2023 | |
| WO | WO-2023004087 A2 | 1/2023 | |
| WO | WO-2023278502 A1 | 1/2023 | |
| WO | WO-2023284789 A1 | 1/2023 | |
| WO | WO-2023147472 A1 | 8/2023 | |
| WO | WO2023183468 A2 | 9/2023 | |
| WO | WO2023235878 A2 | 12/2023 | |
| WO | WO2023244983 A1 | 12/2023 | |
| WO | WO2023250441 A2 | 12/2023 | |

OTHER PUBLICATIONS

Friedland et al.: Development and Clinical Validation of a blood test for early detection of colorectal adenomas and cancer. Abstract 32305, Poster ASCO GI Meeting [1-1] (2021).

Frommer et al. A genomic sequencing protocol that yields a positive display of 5-methylcytosine residues in individual DNA strands. PNAS USA 89:1827-1831 (1992).

Golub et al. Molecular classification of cancer: Class discovery and class prediction by gene expression monitoring, Science, American Association for the Advancement of Science, 286:5439 (Oct. 15, 1999).

Herman, J.G., et al., "Methylation-Specific PCR: A Novel PCR Assay for Methylation Status of CpG Islands." Proceedings of the National Academy of Science USA 93:9821-9826, Sep. 1996.

Kourou et al.: Machine learning applications in cancer prognosis and prediction. Comput Struct Biotechnol J.13:8-17 (2014).

Liu et al.: An individualized predictor of health and disease using paired reference and target samples. BMC Bioinformatics 17:47 [1-15] (2016).

Liu et al. Bisulfite-Free Direct Detection of 5-Methylcytosine and 5-Hydroxymethylcytosine at Base Resolution. Nature Biotechnology 37(4):424-429 (2019).

Manghnani et al.: METCC: METric learning for Confounder Control Making distance matter in high dimensional biological analysis. arXiv:1812.03188v1 [cs.LG] [1-10] (2018).

PCT/US2021/063337 International Search Report and Written Opinion dated May 3, 2022.

Schutsky et al. Nondestructive, Base-Resolution Sequencing of 5-Hydroxymethylcytosine Using a DNA Deaminase. Nature Biotechnology 36(11):1083-1090 (2018).

Singh, et al. "Gene expression correlates of clinical prostate cancer behavior." Cancer Cell. vol. 1, pp. 203-209 (2002).

Wan et al.: Machine learning enables detection of early-stage colorectal cancer by whole-genome sequencing of plasma cell-free DNA. bioRxiv prePrint URL:https://doi.org/10.1101/478065 [1-22] (2018).

Yu et al.: Tet-assisted bisulfite sequencing of 5-hydroxymethylcytosine. Nat Protoc. 7(12):2159-2170 doi:10.1038/nprot.2012.137 (2012).

Zhang et al. Tet-mediated covalent labelling of 5-methylcytosine for its genome-wide detection and sequencing, Nat Commun. 2013;4:1517.

Ahn et al., Potential early clinical stage colorectal cancer diagnosis using a proteomics blood test panel. Clin Proteomics. 16:34, pp. 1-20 (2019).

Blume et al., Discovery and validation of plasma-protein biomarker panels for the detection of colorectal cancer and advanced adenoma in a Danish collection of samples from patients referred for diagnostic colonoscopy. J Appl Lab Med. 1(2):181-193 (2016).

Chen et al., Development and validation of a panel of five proteins as blood biomarkers for early detection of colorectal cancer. Clin Epidemiol. 9:517-526 (2017).

(56) References Cited

OTHER PUBLICATIONS

Fredolini et al., Systematic assessment of antibody selectivity in plasma based on a resource of enrichment profiles. Sci Rep. 9(1):8324, pp. 1-13 (2019).

Fung et al., Blood-based protein biomarker panel for the detection of colorectal cancer. PLoS One. 10(3):e0120425 (2015).

Harlid et al., A two-tiered targeted proteomics approach to identify pre-diagnostic biomarkers of colorectal cancer risk. Sci Rep. 11(1):5151 pp. 1-12 (2021).

Jones et al., A plasma-based protein marker panel for colorectal cancer detection identified by multiplex targeted mass spectrometry. Clinical Colorectal Cancer 15(2):186-194.e13 (2016).

Surinova et al., Prediction of colorectal cancer diagnosis based on circulating plasma proteins. EMBO Mol Med. 7(9):1166-1178 (2015).

U.S. Appl. No. 18/163,169 Final Office Action dated Oct. 13, 2023.

EP Serial No. 21911901.3 Partial Search Report dated Oct. 9, 2024.

Knuchel, Sarah, et al. Fibroblast surface-associated FGF-2 promotes contact-dependent colorectal cancer cell migration and invasion through FGFR-SRC signaling and integrin avß5-mediated adhesion. Oncotarget 6.16: 14300. (2015).

Korbecki, Jan, et al. Fractalkine/CX3CL1 in neoplastic processes. International journal of molecular sciences 21.10: 3723. (2020).

Li, Jingjing, et al. The role of interleukins in colorectal cancer. International journal of biological sciences 16.13: 2323. (2020).

Messa, Caterina, et al. EGF, TGF-a, and EGF-R in human colorectal adenocarcinoma. Acta Oncologica 37.3: 285-289. (1998).

Spagnoli, Giulio C., et al. FLT3 ligand gene expression and protein production in human colorectal cancer cell lines and clinical tumor specimens. International journal of cancer 86.2: 238-243. (2000).

\* cited by examiner

MARKERS FOR THE EARLY DETECTION OF COLON CELL PROLIFERATIVE DISORDERS

CROSS-REFERENCE TO RELATED APPLICATIONS

This application is a continuation of International Patent Application No. PCT/US2021/063337, filed Dec. 14, 2021, which claims the benefit of U.S. Provisional Patent Application No. 63/128,545, filed Dec. 21, 2020, each of which is incorporated by reference herein in its entirety.

FIELD

This disclosure is related to biomarkers and methods for the early identification of colon cell proliferative disorders including advanced adenoma and colorectal cancer.

BACKGROUND

Colorectal cancer (CRC) is the leading cause of cancer-related mortality in the western world. Although CRC is one of the best characterized solid tumors, CRC continues to be one of the main causes of death in developed countries because of late diagnosis. Among other reasons, late diagnosis of patients is due to the fact that diagnostic tests, such as colonoscopy, are performed too late. Deaths from CRC can be prevented through effective and early screening.

SUMMARY

The present disclosure provides methods and systems directed to protein profiling of biological samples associated with CRC detection and disease progression. Studies described herein enable determination of the presence of a specific protein signature of CRC showing the presence of specific biomarkers of the colon cell proliferative disorders with potential for detecting colon cell proliferative disorders, stratifying patient populations, and classifying populations using plasma from subjects with a colon cell proliferative disorder with high specificity and high sensitivity.

In an aspect, the present disclosure provides a predetermined protein panel characteristic of a colon cell proliferative disorder comprising at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII (IL1R2), HGFR, IL-6ra, OPN, Tenascin-C (TNC), Thrombospondin-2 (THBS2), uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA.

In some embodiments, the panel comprises FLT3L, CEACAM5, IL-6RA, ORM, or a combination thereof.

In some embodiments, the panel comprises FLT3L, CEACAM5, IL-6RA, ORM, IL-8, AGP, IL-1RT2, TNC, GDF-15, or a combination thereof.

In some embodiments, the panel comprises FLT3L, CEACAM5, IL-6RA, ORM, IL-8, AGP, IL-1RT2, TNC, GDF-15, AGRP, Haptoglobin, ANGPTL4, FGF-23, Complement component C2, ORM2, FGF-23, MUC-16, EGF, or a combination thereof.

In some embodiments, the panel comprises FLT3L, CEACAM5, IL-6, IL-8, MIP-3a, IL-1RT2, TNC, or any combination thereof.

In some embodiments, the panel comprises FLT3L, CEACAM5, IL-6, IL-8, MIP-3a, IL-1RT2, TNC, HGFR, THBS2, CA125 (MUC-16), CA19-9, CA15-3 (MUC-1), or any combination thereof.

In some embodiments, the panel comprises total PSA.

In some embodiments, the panel is configured to distinguish healthy subjects, subjects with benign colon polyp, subjects with advanced adenoma, or subjects with colorectal cancer.

In some embodiments, the panel is configured to indicate advanced adenoma and comprises: 1) FLT3L, CEACAM5, IL-6RA, and ORM; 2) FLT3L, CEACAM5, IL-6RA, CEA, ORM, IL-8, AGP, IL-1RT2, TNC, and GDF-15; or 3) FLT3L, CEACAM5, IL-6RA, CEA, ORM, IL-8, AGP, IL-1RT2, TNC, GDF-15, AGRP, Haptoglobin, ANGPTL4, FGF-23, Complement component C2, ORM2, FGF-23, MUC-16, EGF, p00738, or a combination thereof.

In some embodiments, the panel is configured to indicate colorectal cancer and comprises: 1) FLT3L, CEACAM5, and IL-6RA; 2) FLT3L, CEACAM5, IL-6RA, IL-8, IL-1RT2, TNC, and a combination thereof; or 3) proteins selected from the group consisting of FLT3L, CEACAM5, IL-6RA, IL-8, AFP, IL-1RT2, TNC, MUC-16, EGF, and a combination thereof.

In some embodiments, the colon cell proliferative disorder is selected from the group consisting of adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas.

In another aspect, the present disclosure provides a classifier configured to distinguish a population of healthy subjects from subjects with a colon cell proliferative disorder comprising: sets of measured values representative of proteins from a predetermined protein panel characteristic of the colon cell proliferative disorder, wherein the sets of measured values are obtained from protein expression data from samples of healthy subject and samples of subjects having a colon cell proliferative disorder, wherein the measured values are used to generate a set of features corresponding to properties of the protein expression data, wherein the sets of features is computer-processed using a machine learning or statistical model, and wherein the machine learning or statistical model provides a feature vector useful as a classifier capable of distinguishing a population of healthy subjects from subjects having the colon cell proliferative disorder.

In some embodiments, the predetermined protein panel comprises at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA.

In some embodiments, the panel comprises FLT3L, CEACAM5, IL-6RA, ORM, or a combination thereof.

In some embodiments, the panel comprises FLT3L, CEACAM5, IL-6RA, ORM, IL-8, AGP, IL-1RT2, TNC, GDF-15, or a combination thereof.

In some embodiments, the panel comprises FLT3L, CEACAM5, IL-6RA, ORM, IL-8, AGP, IL-1RT2, TNC, GDF-15, AGRP, Haptoglobin, ANGPTL4, FGF-23, Complement component C2, ORM2, FGF-23, MUC-16, EGF, or a combination thereof.

In some embodiments, the panel comprises FLT3L, CEACAM5, IL-6, IL-8, MIP-3a, IL-1RT2, TNC or a combination thereof.

In some embodiments, the panel comprises FLT3L, CEACAM5, IL-6, IL-8, MIP-3a, IL-1RT2, TNC, HGFR, THBS2, CA125 (MUC-16), CA19-9, CA15-3 (MUC-1), or a combination thereof.

In some embodiments, the panel comprises total PSA.

In some embodiments, the classifier is configured to distinguish healthy subjects, subjects with benign colon polyp, subjects with advanced adenoma, or subjects with colorectal cancer.

In some embodiments, wherein the panel is configured to indicate advanced adenoma and comprises: 1) proteins selected from FLT3L, CEACAM5, IL-6RA, ORM, or a combination thereof 2) proteins selected from FLT3L, CEACAM5, IL-6RA, CEA, ORM, IL-8, AGP, IL-1RT2, TNC, GDF-15, or a combination thereof; or 3) proteins selected from FLT3L, CEACAM5, IL-6RA, CEA, ORM, IL-8, AGP, IL-1RT2, TNC, GDF-15, AGRP, Haptoglobin, ANGPTL4, FGF-23, Complement component C2, ORM2, FGF-23, MUC-16, EGF, p00738, or a combination thereof.

In some embodiments, the panel is configured to indicate colorectal cancer and comprises: 1) FLT3L, CEACAM5, IL-6RA, and a combination thereof; 2) FLT3L, CEACAM5, IL-6RA, IL-8, IL-1RT2, TNC; or 3) proteins selected from FLT3L, CEACAM5, IL-6RA, ORM, IL-8, AGP, IL-1RT2, TNC, MUC-16, EGF, and a combination thereof.

In some embodiments, the colon cell proliferative disorder is selected from the group consisting of adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas.

In another aspect, the present disclosure provides a system comprising a machine learning model classifier for detecting a colon cell proliferative disorder comprising: a computer-readable medium comprising a classifier operable to classify subjects based on a predetermined protein panel; and one or more processors for executing instructions stored on the computer-readable medium.

In some embodiments, the system comprises a classifier configured to distinguish a population of healthy subjects from subjects with a colon cell proliferative disorder comprising: sets of measured values representative of proteins from a predetermined protein panel characteristic of the colon cell proliferative disorder, wherein the sets of measured values are obtained from protein expression data from samples of healthy subject and samples of subjects having a colon cell proliferative disorder, wherein the measured values are used to generate a set of features corresponding to properties of the protein expression data, wherein the sets of features is computer-processed using a machine learning or statistical model, and wherein the machine learning or statistical model provides a feature vector useful as a classifier capable of distinguishing a population of healthy subjects from subjects having the colon cell proliferative disorder.

In some embodiments, the panel comprises at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA.

In some embodiments, the machine learning model is trained using training data obtained from training biological samples, a first subset of the training biological samples identified as corresponding to a subject having a colon cell proliferative disorder and a second subset of the training biological samples identified corresponding to a subject as not having a colon cell proliferative disorder.

In some embodiments, the classifier is provided in a system for detecting a colon cell proliferative disorder comprising: a) a computer-readable medium comprising a classifier operable to classify the subjects based on a protein signature panel; and b) one or more processors for executing instructions stored on the computer-readable medium.

In some embodiments, the system comprises a classification circuit that is configured as a machine learning classifier selected from the group consisting of a deep learning classifier, a neural network classifier, a linear discriminant analysis (LDA) classifier, a quadratic discriminant analysis (QDA) classifier, a support vector machine (SVM) classifier, a random forest (RF) classifier, K nearest neighbor, a linear kernel support vector machine classifier, a first or second order polynomial kernel support vector machine classifier, a ridge regression classifier, an elastic net algorithm classifier, a sequential minimal optimization algorithm classifier, a naive Bayes algorithm classifier, and principal component analysis classifier.

In another aspect, the present disclosure provides a method for determining a protein profile of a biological sample from a subject comprising:
  a) obtaining the biological sample containing proteins from the subject; and
  b) measuring in the biological sample an amount of a protein from a predetermined panel of proteins comprising at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA, thereby providing the protein profile of the subject.

In some embodiments, the predetermined panel of proteins comprises FLT3L, CEACAM5, IL-6RA, ORM, or a combination thereof.

In some embodiments, the predetermined panel of proteins comprises FLT3L, CEACAM5, IL-6RA, ORM, IL-8, AGP, IL-1RT2, TNC, GDF-15, or a combination thereof.

In some embodiments, the predetermined panel of proteins comprises FLT3L, CEACAM5, IL-6RA, ORM, IL-8, AGP, IL-1RT2, TNC, GDF-15, AGRP, Haptoglobin, ANGPTL4, FGF-23, Complement component C2, ORM2, FGF-23, MUC-16, EGF, or a combination thereof.

In some embodiments, the panel comprises FLT3L, CEACAM5, IL-6, IL-8, MIP-3a, IL-1RT2, TNC, or a combination thereof.

In some embodiments, the panel comprises FLT3L, CEACAM5, IL-6, IL-8, MIP-3a, IL-1RT2, TNC, HGFR, THBS2, CA125 (MUC-16), CA19-9, CA15-3 (MUC-1), or a combination thereof.

In some embodiments, the panel comprises total PSA.

In some embodiments, the protein profile is associated with a colon cell proliferative disorder and provides classification of the subject as having the colon cell proliferative disorder.

In some embodiments, the biological sample from the subject is selected from the group consisting of bodily fluids, stool, colonic effluent, urine, blood plasma, blood serum, whole blood, isolated blood cells, cells isolated from the blood, tissue biopsy, and a combination thereof.

In some embodiments, the colon cell proliferative disorder is selected from the group consisting of adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas.

In some embodiments, the method further comprises treating the subject with surgery and/or a therapeutic agent based on the protein profile of the subject.

In another aspect, the present disclosure provides a method for detecting a colon cell proliferative disorder in a subject comprising:
  a) obtaining a biological sample containing proteins from the subject;
  b) measuring in the biological sample an amount of a protein from a predetermined protein panel comprising at least 6 of proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA, thereby providing a protein profile of the subject; and
  c) computer-processing the protein profile into a machine learning model trained to be capable of distinguishing between healthy subjects and subjects with the colon cell proliferative disorder to provide an output value associated with presence or absence of the colon cell proliferative disorder, thereby indicating the presence or absence of the colon cell proliferative disorder in the subject.

In some embodiments, the predetermined panel of proteins comprises FLT3L, CEACAM5, IL-6RA, ORM, or a combination thereof.

In some embodiments, the predetermined panel of proteins comprises FLT3L, CEACAM5, IL-6RA, ORM, IL-8, AGP, IL-1RT2, TNC, GDF-15, or a combination thereof.

In some embodiments, the predetermined panel of proteins comprises FLT3L, CEACAM5, IL-6RA, ORM, IL-8, AGP, IL-1RT2, TNC, GDF-15, AGRP, Haptoglobin, ANGPTL4, FGF-23, Complement component C2, ORM2, FGF-23, MUC-16, EGF, or a combination thereof.

In some embodiments, the panel comprises FLT3L, CEACAM5, IL-6, IL-8, MIP-3a, IL-1RT2, TNC or a combination thereof.

In some embodiments, the panel comprises FLT3L, CEACAM5, IL-6, IL-8, MIP-3a, IL-1RT2, TNC, HGFR, THBS2, CA125 (MUC-16), CA19-9, CA15-3 (MUC-1), or a combination thereof.

In some embodiments, the panel comprises total PSA.

In some embodiments, the protein profile is associated with a colon cell proliferative disorder and provides classification of the subject as having the colon cell proliferative disorder.

In some embodiments, the biological sample from the subject is selected from the group consisting of bodily fluids, stool, colonic effluent, urine, blood plasma, blood serum, whole blood, isolated blood cells, cells isolated from the blood, tissue biopsy, and a combination thereof.

In some embodiments, the colon cell proliferative disorder is selected from the group consisting of adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas.

In some embodiments, the method further comprises administering a treatment to the subject based on the detected colon cell proliferative disorder. In some embodiments, the treatment comprises chemotherapy, radiotherapy, immunotherapy, or surgery.

In another aspect, a method is provided for monitoring minimal residual disease in a subject previously treated for a disease, comprising:
  a) determining a protein profile of a biological sample from the subject using a panel of at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA, thereby generating a baseline protein state;

b) determining a protein profile of a biological sample obtained from the subject at one or more time points after the generating of the baseline protein state, thereby generating a current protein state; and c) determining a difference between the baseline protein state and the current protein state, thereby detecting a change in the minimal residual disease in the subject.

In some embodiments, the minimal residual disease is selected from the group consisting of response to treatment, tumor load, residual tumor post-surgery, relapse, secondary screen, primary screen, and cancer progression. In some embodiments, the method further comprises administering a treatment to the subject based on the detected change in the minimal residual disease in the subject. In some embodiments, the treatment comprises chemotherapy, radiotherapy, immunotherapy, or surgery. A treatment may be selected (e.g., from among a plurality of possible treatment options) and administered to the subject based at least in part on a protein profile of the subject and/or a set of biological traits of the subject. The biological traits may be a measurement, a diagnosis, a prognosis, or a prediction (e.g., determined using a trained machine learning classifier).

In some embodiments, the biological trait comprises malignancy. [0004] In some embodiments, the biological trait comprises a cancer type. In some embodiments, the biological trait comprises a cancer stage. In some embodiments, the biological trait comprises a cancer classification. In some embodiments, the cancer classification comprises a cancer grade. In some embodiments, the cancer classification comprises a histological classification. In some embodiments, the biological trait comprises a metabolic profile. In some embodiments, the biological trait comprises a mutation. In some embodiments, the mutation is a disease-associated mutation. In some embodiments, the biological trait comprises a clinical outcome. In some embodiments, the biological trait comprises a drug response.

In another aspect, a method is provided for determining response of a subject to treatment, comprising:

a) determining a protein profile of a biological sample from the subject using a panel of at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA, thereby generating a baseline protein state;

b) determining a protein profile of a biological sample obtained from the subject at one or more time points after the generating of the baseline protein state, thereby generating a current protein state; and c) determining a difference between the baseline protein state and the current protein state, thereby determining the response of the subject to the treatment.

In some embodiments, the method further comprises administering a treatment to the subject based on the determined response of the subject to the treatment. In some embodiments, the treatment comprises chemotherapy, radiotherapy, immunotherapy, or surgery.

In another aspect, a method is provided for monitoring tumor load of a subject, comprising:

a) determining a protein profile of a biological sample from the subject using a panel of at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA, thereby generating a baseline protein state;

b) determining a protein profile of a biological sample obtained from the subject at one or more time points after the generating of the baseline protein state, thereby generating a current protein state; and c) determining a difference between the baseline protein state and the current protein state, thereby monitoring the tumor load of the subject.

In some embodiments, the method further comprises administering a treatment to the subject based on the tumor load of the subject. In some embodiments, the treatment comprises chemotherapy, radiotherapy, immunotherapy, or surgery.

In another aspect, a method is provided for detecting residual tumor post-surgery of a subject, comprising:

a) determining a protein profile of a biological sample from the subject using a panel of at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA, thereby generating a baseline protein state;

b) determining a protein profile of a biological sample obtained from the subject at one or more time points after the generating of the baseline protein state, thereby generating a current protein state; and c) determining a difference between the baseline protein state and the current protein state, thereby detecting residual tumor post-surgery of the subject.

In some embodiments, the method further comprises administering a treatment to the subject based on the detected residual tumor post-surgery of the subject. In some embodiments, the treatment comprises chemotherapy, radiotherapy, immunotherapy, or surgery.

In another aspect, a method is provided for detecting relapse of a subject, comprising:

a) determining a protein profile of a biological sample from the subject using a panel of at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA, thereby generating a baseline protein state;
b) determining a protein profile of a biological sample obtained from the subject at one or more time points after the generating of the baseline protein state, thereby generating a current protein state; and
c) determining a difference between the baseline protein state and the current protein state, thereby detecting relapse of the subject.

In some embodiments, the method further comprises administering a treatment to the subject based on the detected relapse of the subject. In some embodiments, the treatment comprises chemotherapy, radiotherapy, immunotherapy, or surgery.

In another aspect, a method is provided for performing a secondary screen, based at least in part on a protein profile of a subject.

In another aspect, a method is provided for performing a primary screen, based at least in part on a protein profile of a subject.

In another aspect, a method is provided for monitoring cancer progression of a subject, comprising:
a) determining a protein profile of a biological sample from the subject using a panel of at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA, thereby generating a baseline protein state;
b) determining a protein profile of a biological sample obtained from the subject at one or more time points after the generating of the baseline protein state, thereby generating a current protein state; and
c) determining a difference between the baseline protein state and the current protein state, thereby monitoring cancer progression of the subject.

In some embodiments, the method further comprises administering a treatment to the subject based on the monitored cancer progression of the subject. In some embodiments, the treatment comprises chemotherapy, radiotherapy, immunotherapy, or surgery.

In some embodiments, the protein profile is indicative of the presence or susceptibility of colorectal cancer at a sensitivity of at least about 25%. In some embodiments, the protein profile is indicative of a presence or susceptibility of colorectal cancer at a sensitivity of at least about 30%. In some embodiments, the protein profile is indicative of the presence or susceptibility of colorectal cancer at a sensitivity of at least about 35%. In some embodiments, the protein profile is indicative of the presence or susceptibility of colorectal cancer at a sensitivity of at least about 40%. In some embodiments, the protein profile is indicative of the presence or susceptibility of colorectal cancer at a sensitivity of at least about 50%. In some embodiments, the protein profile is indicative of the presence or susceptibility of colorectal cancer at a sensitivity of at least about 60%. In some embodiments, the protein profile is indicative of the presence or susceptibility of colorectal cancer at a sensitivity of at least about 70%. In some embodiments, the protein profile is indicative of the presence or susceptibility of colorectal cancer at a sensitivity of at least about 80%. In some embodiments, the protein profile is indicative of the presence or susceptibility of colorectal cancer at a sensitivity of at least about 90%. In some embodiments, the protein profile is indicative of the presence or susceptibility of colorectal cancer at a sensitivity of at least about 95%.

In some embodiments, the protein profile is indicative of the presence or susceptibility of colorectal cancer at a positive predictive value (PPV) of at least about 5%. In some embodiments, the protein profile is indicative of the presence or susceptibility of colorectal cancer at a positive predictive value (PPV) of at least about 10%. In some embodiments, the protein profile is indicative of the presence or susceptibility of colorectal cancer at a positive predictive value (PPV) of at least about 15%. In some embodiments, the protein profile is indicative of the presence or susceptibility of colorectal cancer at a positive predictive value (PPV) of at least about 20%. In some embodiments, the protein profile is indicative of the presence or susceptibility of colorectal cancer at a positive predictive value (PPV) of at least about 25%. In some embodiments, the protein profile is indicative of the presence or susceptibility of colorectal cancer at a positive predictive value (PPV) of at least about 30%. In some embodiments, the protein profile is indicative of the presence or susceptibility of colorectal cancer at a positive predictive value (PPV) of at least about 40%. In some embodiments, the protein profile is indicative of the presence or susceptibility of colorectal cancer at a positive predictive value (PPV) of at least about 50%. In some embodiments, the protein profile is indicative of the presence or susceptibility of colorectal cancer at a positive predictive value (PPV) of at least about 60%. In some embodiments, the protein profile is indicative of the presence or susceptibility of colorectal cancer at a positive predictive value (PPV) of at least about 70%. In some embodiments, the protein profile is indicative of the presence or susceptibility of colorectal cancer at a positive predictive value (PPV) of at least about 80%. In some embodiments, the protein profile is indicative of the presence or susceptibility of colorectal cancer at a positive predictive value (PPV) of at least about 90%. In some embodiments, the protein profile is indicative of the presence or susceptibility of colorectal cancer at a positive predictive value (PPV) of at least about 95%. In some embodiments, the protein profile is indicative of the presence or susceptibility of colorectal cancer at a positive predictive value (PPV) of at least about 99%.

In some embodiments, the protein profile is indicative of the presence or susceptibility of colorectal cancer at a negative predictive value (NPV) of at least about 40%. In some embodiments, the protein profile is indicative of the presence or susceptibility of colorectal cancer at a negative predictive value (NPV) of at least about 50%. In some embodiments, the protein profile is indicative of the presence or susceptibility of colorectal cancer at a negative predictive value (NPV) of at least about 60%. In some embodiments, the protein profile is indicative of the presence or susceptibility of colorectal cancer at a negative predictive value (NPV) of at least about 70%. In some embodiments, the protein profile is indicative of the presence or susceptibility of colorectal cancer at a negative predictive value (NPV) of at least about 80%. In some embodiments, the protein profile is indicative of the presence or susceptibility of colorectal cancer at a negative predictive value (NPV) of at least about 90%. In some embodiments, the protein profile is indicative of the presence or susceptibility of colorectal cancer at a negative predictive value (NPV) of at least about 95%. In some embodiments, the protein profile is indicative of the presence or susceptibility of colorectal cancer at a negative predictive value (NPV) of at least about 99%.

In some embodiments, the trained algorithm determines the presence or susceptibility of colorectal cancer of the subject with an Area Under Curve (AUC) of at least about 0.50. In some embodiments, the trained algorithm determines the presence or susceptibility of colorectal cancer of the subject with an Area Under Curve (AUC) of at least about 0.60. In some embodiments, the trained algorithm determines the presence or susceptibility of colorectal cancer of the subject with an Area Under Curve (AUC) of at least about 0.70. In some embodiments, the trained algorithm determines the presence or susceptibility of colorectal cancer of the subject with an Area Under Curve (AUC) of at least about 0.80. In some embodiments, the trained algorithm determines the presence or susceptibility of colorectal cancer of the subject with an Area Under Curve (AUC) of at least about 0.90. In some embodiments, the trained algorithm determines the presence or susceptibility of colorectal cancer of the subject with an Area Under Curve (AUC) of at least about 0.95. In some embodiments, the trained algorithm determines the presence or susceptibility of colorectal cancer of the subject with an Area Under Curve (AUC) of at least about 0.99.

In some embodiments, the method further comprises presenting a report or a graphical user interface of an electronic device of a user. In some embodiments, the user is the subject, individual or patient.

In some embodiments, the method further comprises determining a likelihood of the determination of a presence or susceptibility of colorectal cancer in the subject, individual, or patient.

In some embodiments, the trained algorithm (e.g., machine learning model or classifier) comprises a supervised or semi-supervised machine learning algorithm. In some embodiments, the supervised machine learning algorithm comprises a deep learning algorithm, a support vector machine (SVM), a neural network, or a Random Forest.

In some embodiments, the method further comprises providing the subject with a therapeutic intervention or administering a treatment to the subject based at least in part on the protein profile or analysis, such as a therapeutic intervention to treat a patient with colorectal cancer (e.g., chemotherapy, radiotherapy, immunotherapy, or surgery).

In some embodiments, the method further comprises monitoring the presence or susceptibility of the colorectal cancer, wherein the monitoring comprises assessing the presence or susceptibility of the colorectal cancer of the subject at a plurality of time points, wherein the assessing is based at least on the presence or susceptibility of the colorectal cancer determined at each of the plurality of time points.

In some embodiments, a difference in the assessment of the presence or susceptibility of the colorectal cancer of the subject among the plurality of time points is indicative of one or more clinical indications selected from the group consisting of: (i) a diagnosis of the presence or susceptibility of the colorectal cancer of the subject, (ii) a prognosis of the presence or susceptibility of the colorectal cancer of the subject, and (iii) an efficacy or non-efficacy of a course of treatment for treating the presence or susceptibility of the colorectal cancer of the subject.

In some embodiments, the method further comprises stratifying the colorectal cancer of the subject by using the trained algorithm to determine a sub-type of the colorectal cancer of the subject from among a plurality of distinct subtypes or stages of colorectal cancer.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Another aspect of the present disclosure provides a system comprising: a) a computer-readable medium comprising a classifier for distinguishing a population of subjects having a colon cell proliferative disorder from subjects not having the colon cell proliferative disorder based on a protein signature panel using a machine learning model; and b) one or more processors for executing instructions stored on the computer-readable medium.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent that publications and patents or patent applications incorporated by reference contradict the disclosure contained in the specification, the specification is intended to supersede and/or take precedence over any such contradictory material.

BRIEF DESCRIPTION OF THE DRAWINGS

Examples of the present disclosure will now be described, by way of example only, with reference to the attached Figures. The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
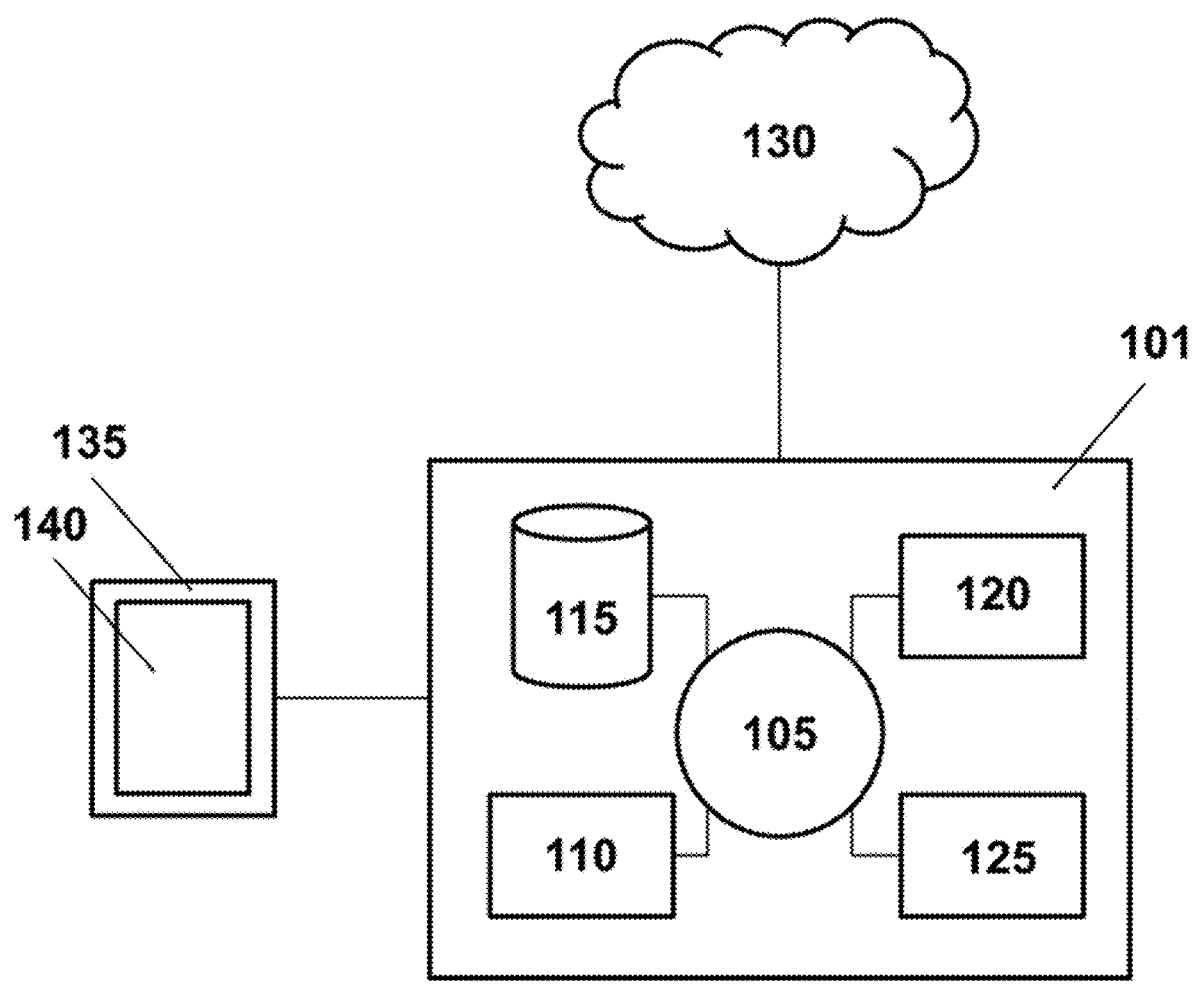
FIG. 1 provides a schematic of a computer system that is programmed or otherwise configured with the machine learning models and classifiers in order to implement methods provided herein.

While various embodiments of the invention have been shown and described herein, it will be obvious to those having ordinary skill in the art that such embodiments are provided by way of example only. Numerous variations, changes, and substitutions can occur to those having ordinary skill in the art without departing from the invention. It should be understood that various alternatives to the embodiments of the invention described herein can be employed.

CRC is the leading cause of cancer-related mortality in the western world. Although CRC is one of the best characterized solid tumors, CRC continues to be one of the main causes of death in developed countries because of late diagnosis. Among other reasons, late diagnosis of patient is due to the fact that diagnostic tests, such as colonoscopy, are performed too late. Deaths from CRC can be prevented through effective screening. Currently, there is no universal specific screening test or panel that helps direct clinical decision making. Cancer screening and monitoring improve survival outcomes because early detection enables for elimination of the cancer before its growth and spread. In CRC, for instance, colonoscopies play a role in improving early diagnosis. Unfortunately, patient compliance rates are low, and screening is conducted below recommended regularity due to the invasiveness of the procedure. The implementation of non-invasive and simpler diagnostic methods which enable the early detection of colorectal neoplasia may be based on identifying proteins detectable in serum or plasma. Non-invasive approaches may be the foundation of more compliant and earlier screening tests for colorectal neoplasia.

Recent studies support the presence of tumor-related antigens in patients with cancer. Since tumorigenesis is associated with changes in the structure or expression of self-proteins in tumor cells, these changes may serve as potential immunological markers of cancer.

The existence of cancer and tumors in humans is also associated with the presence of proteins in the serum from patients with cancer. Proteins can be detected in early stages of the disease, even before the cancer can be detected by means of other techniques, indicating the potential of these proteins as biomarkers of the disease. These proteins can either be affected by expression level changes, isolated mutations, can have anomalous folding, overexpression, aberrant glycosylation, can be truncated, or undergo aberrant degradation.

Therefore, protein biomarkers may enable the diagnosis of colon neoplasia, classification of colon neoplasia in different stages (such as adenoma or tumor progression), prognosis of the progress of the disease, evaluation of disease response to treatment, and detection of the recurrence or the dissemination of colon neoplasia, by means of a simple, effective, and non-invasive method. The diagnostic potential of proteins associated with colon neoplasia may be useful in the early detection, diagnosis, and prognosis of colon neoplasia.

The present disclosure relates generally to cancer detection and disease monitoring. More particularly, the present disclosure relates to cancer-related protein detection and disease monitoring in colon cell proliferative disorders such as early-stage colorectal cancer. Specifically, circulating protein signature panels and uses thereof are provided for identifying human subjects having, or at risk of developing, colon cell proliferative disorders such as colorectal cancer (CRC) and/or colorectal adenomas (CA), for example, advanced colorectal adenomas (AA). Further disclosed herein are tumor associated proteins in a subject that are indicative of the presence of a colon cell proliferative disorder, or a high risk of developing a colon cell proliferative disorder, for example, when the subject has a colorectal lesion.

Some embodiments of the disclosure provide proteins that are differentially abundant in a sample of a subject having colon cell proliferative disorder, or having a high risk of developing colon cell proliferative disorder, as compared to the corresponding sample of a subject not having colon cell proliferative disorder, or having low risk of developing colon cell proliferative disorder. In some embodiments, each of the subjects having a high risk of developing colon cell proliferative disorder and the subjects having a low risk of developing colon cell proliferative disorder have a non-invasive precursor lesion arising within colorectal mucosa (hereinafter, colorectal lesion). The proteins that are present at different abundances in a sample of a healthy subject and a subject having colon cell proliferative disorder can be used as biomarkers for diagnosis, treatment, and/or prevention of colon cell proliferative disorder.

In some embodiments, the method further comprises comparing the protein profile of the biological sample of the subject against a database of reference protein profiles from healthy subjects; and determining that the subject has an increased risk of having a colon cell proliferative disorder based at least in part on measuring a change of at least 5%, at least 10%, at least 15%, at least 20%, at least 25%, at least 30%, at least 35%, at least 40%, at least 45%, or at least 50% in protein expression level of the protein profile relative to the reference protein profiles.

Machine learning approaches may be used to featurize the protein data derived from a biological sample to identify a panel of informative proteins. The identified panel of informative proteins for a colon cell proliferative disorder may be useful to train a classifier model useful for distinguishing samples from healthy subjects and subjects having a colon cell proliferative disorder.

To identify proteins that are informative for the methods and classifiers described herein, the plasma from subjects with colon cell proliferative disorders, and the plasma of subjects without colon cell proliferative disorders (control plasma or reference plasma) have been examined for the purpose of identifying a signature panel of proteins produced by, or differentially expressed in, patients having a colon cell proliferative disorder in response to the colon cell proliferative disorder. To that end, plasma from patients with colon cell proliferative disorders and control plasma were assayed for protein expression to identify biomarkers.

The proteins identified herein can be used to identify subjects that have colon cell proliferative disorder to distinguish them from subjects that do not have colon cell proliferative disorder, to identify subjects having a higher risk of developing colon cell proliferative disorder to distinguish them from subjects that have a lower risk of developing colon cell proliferative disorder, or to identify subjects having a colon cell proliferative disorder precursor lesion. Thus, these proteins can be used as an adjunctive tool to guide decisions regarding monitoring, treatment, and management of a colon cell proliferative disorder.

Certain other embodiments of the disclosure provide a machine learning model classifier trained on the proteins described herein that are expressed in a plasma sample of a healthy subject and a plasma sample from a subject having colon cell proliferative disorder. Training a machine learning model provides a classifier having a predetermined set of protein biomarkers (a "protein panel" or "signature panel") useful for classifying a healthy subject or a subject having a colon cell proliferative disorder. In an example, a method is provided for a blood-based, minimally-invasive protein assay that can be used in a subject having a colorectal lesion to assess histologic severity. In another embodiment, the proteins indicative of colon cell proliferative disorder are detected in cell-free samples from a subject. Bodily fluid samples from a subject such as whole blood, plasma, or serum containing cell-free molecules such as proteins. As such, provided herein are proteins that can be used to differentiate between the presence or absence of colon cell proliferative disorder, high-risk or low-risk colorectal lesions that warrant treatment such as, surgical resection, immunotherapy, radiation, or chemotherapy, and identify low-risk colorectal lesions that can be monitored. Monitoring and confirmation of the presence of a colon cell proliferative disorder or lesions can be carried out, for example, by colonoscopy, ultrasound, MM, or CT scan.

In some embodiments, disclosed herein is a predetermined panel of plasma protein biomarkers that is used for the early detection of colorectal proliferation disorders and relating to the early detection of CRC. The predetermined protein panel can be used in a classifier that is indicative of a cell proliferation disorder such as advanced adenoma or colorectal cancer.

In other embodiments, disclosed herein are detection, diagnostic, and treatment-related methods. Plasma from patients may be screened for proteins of a predetermined panel as an indication of colorectal proliferation disorders.

Described herein are methods for screening or identifying subjects having, or at risk of having, a colon cell proliferative disorder based on an expression profile or abundance of proteins that are up-regulated or over-expressed in subjects suffering from a colon cell proliferative disorder. Further described herein are methods for obtaining data useful for diagnosis of a colon cell proliferative disorder in a subject, for example, a human subject.

A colon cell proliferative disorder may be of any tumor stage (e.g., TX, T0, Tis, T1, T2, T3, T4); any regional lymph node or distant metastasis stage (e.g., NX, N0, N1, M0, M1); any stage (e.g., Stage 0 (Tis, N0, M0), Stage IA (T1, N0, M0), Stage IIA (T3, N0, M0), Stage IIB (T1-3, N1, M0), Stage III (T4, Any N, M0), or Stage IV (Any T, Any N, M1)); resectable; locally advanced (unresectable); or metastatic.

Current screening tools may face challenges due to false positive and false negative results, and specificity and sensitivity. An ideal cancer screening tool may have a high Positive Predictive Value (PPV), which minimizes unnecessary investigations (low false positives) but detects a vast majority of cancers (low false negative). Another key compromise is "detection sensitivity", distinct from test sensitivity, which is the lower limit of detecting a tumor based on size. Allowing a tumor to grow to a size large enough to release circulating tumor markers at detectable levels defeats the purpose of early detection and prevention of cancer progression. Hence, the present disclosure addresses a need for highly sensitive and effective blood-based screens for early diagnosis of colorectal cancer.

The detection of circulating tumor DNA, also referred to as a "liquid biopsy," enables the detection and informative investigation of tumors in a non-invasive manner. Identification of tumor specific mutations in these liquid biopsies may be used to diagnose, e.g., colon, breast, and prostate cancers. However, due to the high background of normal (i.e., non-tumor-derived) DNA present in circulation, these techniques may be limited in sensitivity. Thus, there remains a need for more sensitive and specific screening tools for detecting early-stage or low tumor-burden colorectal cancer tumor markers for relapse screening and primary screening of at-risk populations. Circulating proteins to tumor-associated antigens provide another source of informative biomarkers in the liquid biopsy sample that may be used in the machine learning models described herein.

The present disclosure provides methods and systems directed to profiling circulating proteins associated with a colon cell proliferative disorder and progression thereof, for example, a colorectal cancer. Those proteins that are indicative of the presence of a colon cell proliferative disorder or a high risk of developing the colon cell proliferative disorder may be used for diagnosing, treating, or preventing progression of a colon cell proliferative disorders as early as possible, for example, when a subject only has a colorectal lesion. Further provided herein are kits and methods for diagnosing colon cell proliferative disorders or assessing the risk of developing colon cell proliferative disorders in a subject, particularly, when the subject has a colorectal lesion.

In an aspect, provided herein are methods that use a panel of proteins useful for distinguishing samples from subjects based on a disease status. In other aspects, provided herein are methods, assays, and kits directed to detecting, differentiating, and distinguishing a colon cell proliferative disorder using a panel of proteins. Non-limiting examples of colon cell proliferative disorder include adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas.

In some embodiments, the method comprises the use of one or more proteins selected as markers for the differentiation, detection, and distinguishing of a colon cell proliferative disorder.

Definitions

As used in the specification and claims, the singular form "a", "an", and "the" include plural references unless the context clearly dictates otherwise. For example, the term "a nucleic acid" includes a plurality of nucleic acids, including mixtures thereof.

As used herein, the term "subject" generally refers to an entity or a medium that has testable or detectable genetic information. A subject can be a person, individual, or patient. A subject can be a vertebrate, such as, for example, a mammal. Non-limiting examples of mammals include humans, simians, farm animals, sport animals, rodents, and pets. The subject can be a person that has cancer or is suspected of having cancer. The subject may be displaying a symptom indicative of a health, physiological state, or condition of the subject, such as a cancer or other disease, disorder, or condition of the subject. As an alternative, the subject can be asymptomatic with respect to such health or physiological state or condition.

As used herein, the term "sample" generally refers to a biological sample obtained from or derived from one or more subjects. Biological samples may be cell-free biological samples or substantially cell-free biological samples, or may be processed or fractionated to produce cell-free biological samples. For example, cell-free biological samples may include cell-free ribonucleic acid (cfRNA), cell-free deoxyribonucleic acid (cfDNA), cell-free fetal DNA (cffDNA), proteins, antibodies, plasma, serum, urine, saliva, amniotic fluid, and derivatives thereof. Cell-free biological samples may be obtained or derived from subjects using an ethylenediaminetetraacetic acid (EDTA) collection tube, a cell-free RNA collection tube (e.g., Streck® RNA Complete BCT®), or a cell-free DNA collection tube (e.g., Streck® Cell-Free DNA BCT®). Cell-free biological samples may be derived from whole blood samples by fractionation (e.g., by differential centrifugation). Biological samples or derivatives thereof may contain cells. For example, a biological sample may be a blood sample or a derivative thereof (e.g., blood collected by a collection tube or blood drops).

As used herein, the term "cell-free sample" generally refers to a biological sample that is substantially devoid of intact cells. A cell-free sample may be derived from a biological sample that is itself substantially devoid of cells or may be derived from a sample from which cells have been removed. Non-limiting examples of cell-free samples include those derived from blood, serum, plasma, urine, semen, sputum, feces, ductal exudate, lymph, and recovered lavage.

As used herein, the term "colon cell proliferative disorder" generally refers to a disorder or disease that comprises disordered or aberrant proliferation of cells in the colon or rectum. Non-limiting examples of colon cell proliferative disorders include adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas. As used herein, the abbreviation "CRC" is used to identify biological samples from a subject diagnosed with colorectal cancer. As used herein, the abbreviation "AA" is used to identify samples from a subject diagnosed with at least one advanced adenoma. As used herein, the abbreviation "NAA" is used to identify samples from a subject diagnosed with a colorectal tumor that is benign and not an advanced adenoma or colorectal cancer.

As used herein, the term "colorectal cancer" is a medical condition generally characterized by cancer of cells of the intestinal tract below the small intestine (i.e., the large intestine (colon), for example, the cecum, ascending colon, transverse colon, descending colon, sigmoid colon, and rectum).

As used herein, the term "colorectal adenoma" generally refers to adenomas of the colon, also called adenomatous polyps, which is a benign and pre-cancerous stage of the colorectal cancer. Colorectal adenomas may be indicative of a high risk of progression to colorectal cancer.

As used herein, the term "advanced colorectal adenoma" generally refers to adenomas having a size of at least 10 mm or histologically having high grade dysplasia or a villous component higher than 20%.

As used herein, the term "at risk of developing a colon cell proliferative disorder" or "high risk of developing a colon cell proliferative disorder" generally refers to a subject having an increased risk of developing a colon cell proliferative disorder in the near future as compared to a subject not having the colon cell proliferative disorder or having a low risk of developing the colon cell proliferative disorder in the near future. As used herein, the term "near future" refers to a duration of about 1 month to about 2 years, about 6 months to about 18 months, or about 1 year.

As used herein, the terms cancer "type" and "subtype" generally are used relatively herein, such that one "type" of cancer, such as breast cancer, may be "subtypes" based on, e.g., stage, morphology, histology, gene expression, receptor profile, mutation profile, aggressiveness, prognosis, and malignant characteristics. Likewise, "type" and "subtype" may be applied at a finer level, e.g., to differentiate one histological "type" into "subtypes", e.g., defined according to mutation profile or gene expression. Cancer "stage" is also used to refer to classification of cancer types based on histological and pathological characteristics relating to disease progression.

The term "neoplasm" generally refers to any new and abnormal growth of tissue. Thus, a neoplasm can be a premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells. The term "colorectal neoplasm-specific marker" refers to any biological material that can be used to indicate the presence of a colorectal neoplasm (e.g., a premalignant colorectal neoplasm or a malignant colorectal neoplasm).

As used herein, the term "healthy" generally refers to subject not having a colorectal cell proliferation disorder. While health is a dynamic state, as used herein, the term refers to the pathological state of a subject lacking a disease state that reference is being made to in a particular statement. In one example, when referring to a signature panel capable of classifying subjects with colorectal cancer, a healthy individual, a healthy sample, or sample from a healthy individual refers to an individual lacking colorectal cancer (CRC), advanced adenoma (AA), or benign adenoma (NAA). As used herein, the abbreviation "NAA" is used to identify samples from individuals evaluated to be negative for colorectal tumors and as such, in some embodiments, samples identified as NAA are included in the healthy sample group. While other diseases or states of health may be present in that subject, as used herein, the term "healthy" indicates the lack of a stated disease for comparison or classification purposes between subjects having and lacking a disease state being discussed.

The term "minimal residual disease" or "MRD" generally refers to the small number of cancer cells in the body of a subject after cancer treatment. MRD testing may be performed to determine effectiveness of a cancer treatment and to guide further treatment plans.

As used herein, the term "screening" generally refers to examination or testing of a population of subjects at risk of suffering from a colorectal cancer or colorectal adenoma, with the objective of discriminating healthy subjects from subjects who are suffering from an undiagnosed colorectal cancer or colorectal adenoma or subjects at high risk of suffering from said indications.

As used herein, the terms "minimally-invasive biological sample" or "non-invasive sample" generally refer to any sample which is taken from the body of the patient without the need of instruments, other than fine needles used for obtaining blood from a subject. In some embodiments, minimally-invasive biological samples include blood, serum, or plasma samples.

As used herein, the terms "up-regulated" or "over-expressed" generally refer to an increase in an expression level with respect to a given "threshold value" or "cutoff value" by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more than 150%.

As used herein, the terms "threshold value" or "cutoff value", when referring to the expression levels, generally refer to a reference expression level indicative that a subject is likely to suffer from colorectal cancer or colorectal adenoma with a given sensitivity and specificity if the expression levels of the subject are above said threshold or cut-off or reference levels.

As used herein, the term "kit" is not limited to any specific device and includes any device suitable for implementing systems and methods of the present disclosure such as, but not limited to, microarrays, bioarrays, biochips, biochip arrays, or bead-based assays.

Assaying Samples

The cell-free biological samples may be obtained or derived from a human subject. The cell-free biological samples may be stored in a variety of storage conditions before processing, such as different temperatures (e.g., at room temperature, under refrigeration or freezer conditions, e.g., at 25° C., at 4° C., at −18° C., −20° C., or at −80° C.) or different suspensions (e.g., EDTA collection tubes, cell-free RNA collection tubes, or cell-free DNA collection tubes).

The cell-free biological sample may be from a subject with a cancer, a subject that is suspected of having a cancer, or a subject that does not have or is not suspected of having a cancer.

The cell-free biological sample may be obtained before and/or after treatment of a subject with the cancer. Cell-free biological samples may be from a subject during a treatment or a treatment regime. Multiple cell-free biological samples may be from a subject to monitor the effects of the treatment over time. The cell-free biological sample may be taken from a subject known or suspected of having a cancer for which a definitive positive or negative diagnosis is not available via clinical tests. The sample may be taken from a subject suspected of having cancer. The cell-free biological sample may be taken from a subject experiencing unexplained symptoms, such as fatigue, nausea, weight loss, aches and pains, weakness, or bleeding. The cell-free biological sample may be taken from a subject having explained symptoms. The cell-free biological sample may be taken from a subject at risk of developing a cancer due to factors such as familial history, age, hypertension or pre-hypertension, diabetes or pre-diabetes, overweight or obesity, environmental exposure, lifestyle risk factors (e.g., smoking, alcohol consumption, or drug use), or presence of other risk factors.

The cell-free biological sample may contain one or more analytes capable of being assayed, such as cell-free ribonucleic acid (cfRNA) molecules suitable for assaying to generate transcriptomic data, cell-free deoxyribonucleic acid (cfDNA) molecules suitable for assaying to generate genomic data, protein molecules suitable for assaying to generate proteomic data, or a mixture or combination thereof.

After obtaining a cell-free biological sample from the subject, the cell-free biological sample may be processed to generate datasets indicative of a colon cell proliferative disorder of the subject. For example, a presence, absence, or quantitative assessment of protein molecules of the cell-free biological sample at a panel of proteins. Processing the cell-free biological sample from the subject may include: (i) subjecting the cell-free biological sample to conditions that are sufficient to isolate, enrich, or extract a plurality of protein, and (ii) assaying the plurality of protein molecules to generate the dataset.

The biological sample may be used directly in an assay for detecting one or more proteins to generate a protein profile for the sample. In some embodiments, the biological sample may be enriched for proteins before assaying (e.g., using protein-conjugated microbeads). In some embodiments, the biological sample is a plasma sample and is protein-enriched. The biological sample may be assayed with various laboratory methodologies to determine the presence and/or concentration or level of one or more proteins in the biological sample. In some embodiments, such approaches may include, but are not limited to, mass spectrometry, protein microarrays, high-density protein microarrays, e.g., CDI proteome arrays, ELISA, Meso Scale Discovery (e.g., Pacific Biolabs), bead-based immunoassays (e.g., Luminex® magnetic bead-based capture assay), secondary fluoro-antibody assays, DNA-antibody conjugates or antibody-metal conjugates (e.g., mass cytometry, CyTOF), HD-X™ and SR-X™ Ultra-Sensitive Biomarker Detection Systems (e.g., Quanterix®), aptamer based oligo-hybridization MEMS (e.g., Somalogic), flow cytometry, FirePlex® particle technology (e.g., Abcam®), or combinations thereof to determine the protein profile of a biological sample from a subject.

Signature Panels

The present disclosure provides methods and systems to analyze biological samples to obtain measurable features from a combination of protein molecules identified in the sample that are associated with the development of a colon cell proliferative disorder. The collection of identified protein molecules described herein possess informative value in creating classifiers for, and in models of, detection for colon cell proliferative disorders or a stage thereof. While the identified protein molecules may be informative and useful individually, the protein molecules may be used in combinations described herein to form a signature panel where the signature is characteristic of a colon cell proliferative disorder or a stage thereof. The features from the signature panel may be processed using a trained algorithm (e.g., a machine learning model) to create a classifier configured to stratify a population of subjects with a colon cell proliferative disorder. The methods are characterized by using one or more protein described in the signature panels. In some embodiments, a signature panel of at least 3 proteins is useful for the classifiers and methods described herein.

The protein signature panels described herein enables a quick and specific analysis of specific protein associated with colon cell proliferative disorders. The signature panels as described and employed in the methods herein may be used for the improved diagnosis, prognosis, treatment selection, and monitoring (e.g., treatment monitoring) of colon cell proliferative disorders.

The signature panels and methods provide significant improvements over current approaches to detect early-stage colon cell proliferative disorders from bodily fluid samples such as whole blood, plasma, or serum. Current methods used to detect and diagnose colon cell proliferative disorders include colonoscopy, sigmoidoscopy, and fecal occult blood colon cancer. In comparison to these methods, the methods provided herein may be much less invasive than colonoscopy, and equally, if not more sensitive, than sigmoidoscopy, fecal immunochemical test (FIT), and fecal occult blood test (FOBT). Methods provided herein may provide significant advantages in terms of sensitivity and specificity due to the advantageous combination of using a protein panel and highly sensitive assay techniques.

The present disclosure provides methods and systems directed to profiling of proteins associated with colon cell proliferative disorder detection and disease progression. To identify proteins that are informative for the methods and classifiers described herein, plasma from patients with colon cell proliferative disorders and plasma of subjects without colon cell proliferative disorders (control plasma or reference plasma) have been examined to identify a signature panel of proteins produced by patients having a colon cell proliferative disorder in response to said colon cell proliferative disorder and respective reactive proteins. To that end, plasma from patients with colon cell proliferative disorders and control plasma may be tested using high-density antibody microarrays. Antibody microarrays offer a series of advantages with respect to other approaches used for identifying proteins: i) the proteins printed in the array are known beforehand, thereby preventing a subsequent identification and eliminating the possible selection of mimotopes, and ii) there is no predisposition to select any protein because the proteins are all printed at a similar concentration. This combination of factors results in a high sensitivity for identifying biomarkers.

The proteins identified herein can be used to identify subjects that have colon cell proliferative disorder to distinguish them from subjects that do not have colon cell proliferative disorder, or to identify subjects having a higher risk of developing colon cell proliferative disorder to distinguish them from subjects that have a lower risk of developing colon cell proliferative disorder, or to identify subjects having a colon cell proliferative disorder precursor lesion. Thus, these proteins can be used as an adjunctive tool to guide decisions regarding monitoring, treatment, and management of a colon cell proliferative disorder.

In some embodiments, disclosed herein is a panel of plasma protein biomarkers useful for the early detection of colorectal proliferation disorders and relating to the early-detection of colorectal cancer.

In other embodiments, disclosed herein are detection, diagnostic, and treatment-related methods. Plasma from patients is screened for tumor-associated proteins or tumor-derived proteins as an indication of colorectal proliferation disorders.

In an aspect, the present disclosure provides a protein panel characteristic of a colon cell proliferative disorder comprising at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA.

In some embodiments, the panel is useful for indicating samples from subjects with a colon cell proliferative disorder and comprises at least 3 proteins selected from the group consisting of: Complement component C2, Complement component C9, Factor D, Factor I, Complement component C1q, Complement component C3, Complement component C3b, Factor B, and Factor H.

In some embodiments, the protein panel comprises FLT3L, CEACAM5, IL-6RA, CEA, ORM, or any combination thereof.

In some embodiments, the protein panel comprises FLT3L, CEACAM5, IL-6RA, CEA, ORM, IL-8, AGP, IL-1RT2, TNC, GDF-15, or any combination thereof.

In some embodiments, the protein panel comprises FLT3L, CEACAM5, IL-6RA, CEA, ORM, IL-8, AGP, IL-1RT2, TNC, GDF-15, AGRP, Haptoglobin, ANGPTL4, FGF-23, Complement component C2, ORM2, FGF-23, MUC-16, EGF, p00738, or any combination thereof.

In some embodiments, the panel comprises FLT3L, CEACAM5, IL-6, IL-8, MIP-3a, IL-1RT2, TNC, or any combination thereof.

In some embodiments, the panel comprises FLT3L, CEACAM5, IL-6, IL-8, MIP-3a, IL-1RT2, TNC, HGFR, THBS2, CA125 (MUC-16), CA19-9, CA15-3 (MUC-1), or any combination thereof.

In some embodiments, the panel comprises total PSA.

In some embodiments, the protein signature panel is useful in distinguishing healthy subjects, subjects with benign colon polyp, subjects with advanced adenoma, or subjects with colorectal cancer.

In some embodiments, the panel is useful for indicating advanced adenoma and comprises at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA.

In some embodiments, the panel is useful for indicating samples from subjects with advanced adenoma and comprises at least 3 proteins selected from the group consisting of: Complement component C2, Complement component C9, Factor D, Factor I, Complement component C1q, Complement component C3, Complement component C3b, Factor B, and Factor H.

In some embodiments, the panel is useful for indicating colorectal cancer and comprises at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA.

In some embodiments, the panel is useful for indicating samples from subjects with colorectal cancer and comprises at least 3 proteins selected from the group consisting of: Complement component C2, Complement component C9, Factor D, Factor I, Complement component C1q, Complement component C3, Complement component C3b, Factor B, and Factor H.

In some embodiments, a predetermined set of proteins contains at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, or more proteins, such as the proteins described herein. In some embodiments, a predetermined set of proteins contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more proteins, such as the proteins described herein. In some embodiments, a predetermined set of proteins contains proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA. In some embodiments, a predetermined set of proteins contains proteins selected from the group listed in TABLE 2.

In some embodiments, the proteins in the predetermined panel comprise proteins in functional classes such as interleukins, complement pathway mediators, complement proteins, chemokines, growth factors, cytokines, globulin proteins, mucins, and proteinases.

Classifiers, Machine Learning Models & Systems

Machine learning approaches are used to featurize the protein data derived from a biological sample from a subject to identify a panel of informative protein. The identified panel of informative proteins for a colon cell proliferative disorder is useful to train a classifier model useful for distinguishing samples from healthy subjects and subjects having a colon cell proliferative disorder.

Further described herein is a machine learning model classifier trained on the proteins described herein that are expressed in a plasma sample of a healthy subject and a plasma sample from a subject having colon cell proliferative disorder. Training a machine learning model provides a classifier having a predetermined set of protein biomarkers (a "protein panel" or "signature panel") useful for classifying a healthy subject or a subject having a colon cell proliferative disorder. In one example, a method is provided for a blood-based, minimally-invasive protein assay that can be used in a subject having a colorectal lesion to assess histologic severity. In another embodiment, the proteins indicative of a colon cell proliferative disorder are detected in cell-free samples from a subject, for example, bodily fluid samples from a subject, such as whole blood, plasma, or serum. As such, proteins disclosed herein can be used to differentiate between the presence or absence of colon cell proliferative disorder, high-risk colorectal lesions, or low-risk colorectal lesions that warrant treatment such as, surgical resection, immunotherapy, radiation, or chemotherapy, and monitoring of low-risk colorectal lesions. Monitoring and confirmation of the presence of colon cell proliferative disorder or lesions can be carried out, for example, by colonoscopy, ultrasound, MM, or CT scan.

In some examples, protein features are used as input datasets into trained algorithms (e.g., machine learning models or classifiers) to find correlations between protein profile and subject groups (e.g., patient groups). Examples of such patient groups include presence or absence of diseases or conditions, elevated or non-elevated risk of diseases or conditions, stages of diseases or conditions, subtypes of diseases or conditions, responders to treatment vs. non-responders to treatment, and progressors vs. non-progressors. In some examples, feature matrices are generated to compare samples from subjects with known conditions or characteristics. In some embodiments, samples are from healthy subjects, or subjects who do not have any of the known indications and samples from patients known to have cancer.

As used herein, as it relates to machine learning and pattern recognition, the term "feature" generally refers to an individual measurable property or characteristic of a phenomenon being observed. The concept of "feature" is related to that of an explanatory variable used in statistical techniques such as for example, but not limited to, linear regression and logistic regression. Features may be numeric or categorical (e.g., structural features such as strings and graphs are used in syntactic pattern recognition).

As used herein, the term "input features" (or "features") generally refers to variables that are used by the trained algorithm (e.g., a machine learning model or classifier) to predict an output classification (label) of a sample, e.g., a condition, protein identity, protein sequence content (e.g., mutations), suggested data collection operations, or suggested treatments. Values of the variables may be determined for a sample and used to determine a classification.

For a plurality of assays, the system identifies feature sets to input into a trained algorithm (e.g., machine learning model or classifier). The system performs an assay on each biological sample and forms a feature vector from the measured values. The system inputs the feature vector into the machine learning model and obtains an output classification of whether the biological sample has a specified property.

In some embodiments, the machine learning model outputs a classifier capable of distinguishing between two or more groups or classes of subjects or features in a population of subjects or features of the population. In some embodiments, the classifier is a trained machine learning classifier.

In some embodiments, the informative loci or features of biomarkers in a cancer tissue are assayed to form a profile. Receiver-operating characteristic (ROC) curves may be generated by plotting the performance of a particular feature (e.g., any of the biomarkers described herein and/or any item of additional biomedical information) in distinguishing between two populations (e.g., subjects responding and not responding to a therapeutic agent). In some embodiments, the feature data across the entire population (e.g., the cases and controls) are sorted in ascending order based on the value of a single feature.

In various examples, the specified property is selected from the group consisting of: healthy vs. cancer, elevated vs. non-elevated risk of disease, disease subtype, disease stage, progressor vs. non-progressor, and responder vs. non-responder.

In some embodiments, the colon cell proliferative disorder is selected from the group consisting of: adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas.

A. Data Analysis

In some examples, the present disclosure provides a system, method, or kit having data analysis realized in software application, computing hardware, or both. In some examples, the analysis application or system comprises at least a data receiving module, a data pre-processing module, a data analysis module (which can operate on one or more types of protein data), a data interpretation module, or a data visualization module. In some embodiments, the data receiving module includes computer systems that connect laboratory hardware or instrumentation with computer systems that process laboratory data. In some embodiments, the data pre-processing module includes hardware systems or computer software that performs operations on the data in preparation for analysis. Examples of operations that may be applied to the data in the pre-processing module include affine transformations, denoising operations, data cleaning, reformatting, or subsampling. A data analysis module, which may be specialized for analyzing genomic data from one or more genomic materials, can, for example, take assembled genomic sequences and perform probabilistic and statistical analysis to identify abnormal patterns related to a disease, pathology, state, risk, condition, or phenotype. A data interpretation module can use analysis methods, for example, drawn from statistics, mathematics, or biology, to support understanding of the relation between the identified abnormal patterns and health conditions, functional states, prognoses, or risks. A data visualization module can use methods of mathematical modeling, computer graphics, or rendering to create visual representations of data that can facilitate the understanding or interpretation of results.

In some examples, machine learning methods are applied to distinguish samples in a population of samples. In some embodiments, machine learning methods are applied to distinguish samples between healthy and advanced disease (e.g., adenoma) samples.

In some embodiments, the one or more machine learning operations used to train the prediction engine include one or more of: a generalized linear model, a generalized additive model, a non-parametric regression operation, a random forest classifier, a spatial regression operation, a Bayesian regression model, a time series analysis, a Bayesian network, a Gaussian network, a decision tree learning operation, an artificial neural network, a recurrent neural network, a reinforcement learning operation, linear or non-linear regression operations, a support vector machine, a clustering operation, and a genetic algorithm operation.

In some examples, computer processing methods are selected from the group consisting of: logistic regression, multiple linear regression (MLR), dimension reduction, partial least squares (PLS) regression, principal component regression, autoencoders, variational autoencoders, singular value decomposition, Fourier bases, wavelets, discriminant analysis, support vector machine, decision tree, classification and regression trees (CART), tree-based methods, random forest, gradient boost tree, logistic regression, matrix factorization, multidimensional scaling (MDS), dimensionality reduction methods, t-distributed stochastic neighbor embedding (t-SNE), multilayer perceptron (MLP), network clustering, neuro-fuzzy, and artificial neural networks.

In some examples, the methods disclosed herein can include computational analysis on nucleic acid sequencing data of samples from a subject or from a plurality of subjects.

B. Classifier Generation

In an aspect, systems and methods disclosed herein provide a classifier generated based on feature information derived from protein analysis from biological samples containing proteins. The classifier forms part of a predictive engine for distinguishing groups in a population based on features identified in biological samples such as proteins. A collective representation of the protein information in a biological sample can be referred to as a protein profile.

In some embodiments, a classifier is created by normalizing the protein information by formatting similar portions of the protein information into a unified format and a unified scale; storing the normalized protein information in a columnar database; training a prediction engine by applying one or more one machine learning operations to the stored normalized protein information, wherein the prediction engine maps, for a particular population, a combination of one or more features to define at least two classification groups.

In some embodiments, a classifier is created by normalizing the protein information by formatting similar portions of the protein information into a unified format and a unified scale; storing the normalized protein information in a columnar database; training a prediction engine by applying one or more one machine learning operations to the stored normalized protein information features to define at least two classification groups.

In some embodiments, the prediction engine is applied to a population of subjects from which the normalized protein features are obtained and associated with each subject in the population, wherein the output of the prediction engine is assessed to identify a subject associated with a group and classify the subject into a classification group.

Specificity, as used herein, generally refers to "the probability of a negative test among those who are free from the disease." Specificity may be calculated by the number of disease-free persons who tested negative divided by the total number of disease-free subjects.

In some examples, the model, classifier, or predictive test has a specificity of at least 40%, at least 45%, at least 50%, at least 55%, at least 60%, at least 65%, at least 70%, at least 75%, at least 80%, at least 85%, at least 90%, at least 95%, or at least 99%.

Sensitivity, as used herein, generally refers to "the probability of a positive test among those who have the disease." Sensitivity may be calculated by the number of diseased subjects who tested positive divided by the total number of diseased subjects.

In some examples, the model, classifier, or predictive test has a sensitivity of at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

C. Digital Processing Device

In some examples, described herein is a digital processing device or use of the same. In some examples, the digital processing device can include one or more hardware central processing units (CPU), graphics processing units (GPU), or tensor processing units (TPU) that carry out the device's functions. In some examples, the digital processing device can include an operating system configured to perform executable instructions.

In some examples, the digital processing device can optionally be connected to a computer network. In some examples, the digital processing device may be optionally connected to the Internet. In some examples, the digital processing device may be optionally connected to a cloud computing infrastructure. In some examples, the digital processing device may be optionally connected to an intranet. In some examples, the digital processing device may be optionally connected to a data storage device.

Non-limiting examples of suitable digital processing devices include server computers, desktop computers, laptop computers, notebook computers, sub-notebook computers, netbook computers, netpad computers, set-top computers, handheld computers, Internet appliances, mobile smartphones, and tablet computers. Suitable tablet computers can include, for example, those with booklet, slate, and convertible configurations.

In some examples, the digital processing device can include an operating system configured to perform executable instructions. For example, the operating system can include software, including programs and data, which manages the device's hardware and provides services for execution of applications. Non-limiting examples of operating systems include Ubuntu, FreeBSD, OpenBSD, NetBSD®, Linux, Apple® Mac OS X Server®, Oracle® Solaris®, Windows Server®, and Novell® NetWare®. Non-limiting examples of suitable personal computer operating systems include Microsoft® Windows®, Apple® Mac OS X®, UNIX®, and UNIX-like operating systems such as GNU/Linux®. In some examples, the operating system may be provided by cloud computing, and cloud computing resources may be provided by one or more service providers.

In some examples, the device can include a storage and/or memory device. The storage and/or memory device may be one or more physical apparatuses used to store data or programs on a temporary or permanent basis. In some examples, the device may be volatile memory and require power to maintain stored information. In some examples, the device may be non-volatile memory and retain stored information when the digital processing device is not powered. In some examples, the non-volatile memory can include flash memory. In some examples, the non-volatile memory can include dynamic random-access memory (DRAM). In some examples, the non-volatile memory can include ferroelectric random access memory (FRAM). In some examples, the non-volatile memory can include phase-change random access memory (PRAM).

In some examples, the device may be a storage device including, for example, CD-ROMs, DVDs, flash memory devices, magnetic disk drives, magnetic tapes drives, optical disk drives, and cloud computing-based storage. In some examples, the storage and/or memory device may be a combination of devices such as those disclosed herein. In some examples, the digital processing device can include a display to send visual information to a user. In some examples, the display may be a cathode ray tube (CRT). In some examples, the display may be a liquid crystal display (LCD). In some examples, the display may be a thin film transistor liquid crystal display (TFT-LCD). In some examples, the display may be an organic light emitting diode (OLED) display. In some examples, an OLED display may be a passive-matrix OLED (PMOLED) or active-matrix OLED (AMOLED) display. In some examples, the display may be a plasma display. In some examples, the display may be a video projector. In some examples, the display may be a combination of devices such as those disclosed herein.

In some examples, the digital processing device can include an input device to receive information from a user. In some examples, the input device may be a keyboard. In some examples, the input device may be a pointing device including, for example, a mouse, trackball, track pad, joystick, game controller, or stylus. In some examples, the input device may be a touch screen or a multi-touch screen. In some examples, the input device may be a microphone to capture voice or other sound input. In some examples, the input device may be a video camera to capture motion or visual input. In some examples, the input device may be a combination of devices such as those disclosed herein.

D. Non-Transitory Computer-Readable Storage Medium

In some examples, the subject matter disclosed herein can include one or more non-transitory computer-readable storage media encoded with a program including instructions executable by the operating system of an optionally networked digital processing device. In some examples, a computer-readable storage medium may be a tangible component of a digital processing device. In some examples, a computer-readable storage medium may be optionally removable from a digital processing device. In some examples, a computer-readable storage medium can include, for example, CD-ROMs, DVDs, flash memory devices, solid state memory, magnetic disk drives, magnetic tape drives, optical disk drives, cloud computing systems and services, and the like. In some examples, the program and instructions may be permanently, substantially permanently, semi-permanently, or non-transitorily encoded on the media.

E. Computer Systems

The present disclosure provides computer systems that are programmed to implement methods described herein. FIG. 1 shows a computer system 101 that is programmed or otherwise configured to store, process, identify, or interpret patient data, biological data, biological sequences, reference sequences, and protein profiles. The computer system 101 can process various aspects of patient data, biological data, biological sequences, reference sequences, and protein profiles of the present disclosure. The computer system 101 may be an electronic device of a user or a computer system that is remotely located with respect to the electronic device. The electronic device may be a mobile electronic device.

The computer system 101 comprises a central processing unit (CPU, also "processor" and "computer processor" herein) 105, which may be a single core or multi core processor, or a plurality of processors for parallel processing. The computer system 101 also comprises memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120, and peripheral devices 125 are in communication with the CPU 105 through a communication bus (solid lines), such as a motherboard. The storage unit 115 may be a data storage unit (or data repository) for storing data. The computer system 101 may be operatively coupled to a computer network ("network") 130 with the aid of the communication interface 120. The network 130 may be the Internet, an internet and/or extranet, or an intranet and/or extranet that is in communication with the Internet. The network 130 in some examples is a telecommunication and/or data network. The network 130 can include one or more computer servers, which can enable distributed computing, such as cloud computing. The network 130, in some examples, with the aid of the computer system 101, can implement a peer-to-peer network, which may enable devices coupled to the computer system 101 to behave as a client or a server.

The CPU 105 can execute a sequence of machine-readable instructions, which may be embodied in a program or software. The instructions may be stored in a memory location, such as the memory 110. The instructions may be directed to the CPU 105, which can subsequently program or otherwise configure the CPU 105 to implement methods of the present disclosure. Examples of operations performed by the CPU 105 can include fetch, decode, execute, and writeback.

The CPU 105 may be part of a circuit, such as an integrated circuit. One or more other components of the system 101 may be included in the circuit. In some examples, the circuit is an application specific integrated circuit (ASIC).

The storage unit 115 can store files, such as drivers, libraries, and saved programs. The storage unit 115 can store user data, e.g., user preferences and user programs. The computer system 101 in some examples can include one or more additional data storage units that are external to the computer system 101, such as located on a remote server that is in communication with the computer system 101 through an intranet or the Internet.

The computer system 101 can communicate with one or more remote computer systems through the network 130. For instance, the computer system 101 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants. The user can access the computer system 101 via the network 130.

Methods as described herein may be implemented by way of machine (e.g., computer processor) executable code stored on an electronic storage location of the computer system 101, such as, for example, on the memory 110 or electronic storage unit 115. The machine-executable or machine-readable code may be provided in the form of software. During use, the code may be executed by the processor 105. In some examples, the code may be retrieved from the storage unit 115 and stored on the memory 110 for ready access by the processor 105. In some examples, the electronic storage unit 115 may be precluded, and machine-executable instructions are stored on memory 110.

The code may be pre-compiled and configured for use with a machine having a processer adapted to execute the code or may be interpreted or compiled during runtime. The code may be supplied in a programming language that may be selected to enable the code to execute in a pre-compiled, interpreted, or as-compiled fashion.

Aspects of the systems and methods provided herein, such as the computer system 101, may be embodied in programming. Various aspects of the technology may be thought of as "products" or "articles of manufacture" typically in the form of machine (or processor) executable code and/or associated data that is carried on or embodied in a type of machine readable medium. Machine-executable code may be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements comprises optical, electrical, and electromagnetic waves, such as used across physical interfaces between local devices, through wired and optical landline networks and over various airlinks. The physical elements that carry such waves, such as wired or wireless links, optical links or the like, also may be considered as media bearing the software. As used herein, unless restricted to non-transitory, tangible "storage" media, terms such as computer or machine "readable medium" generally refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases described herein. Volatile storage media include dynamic memory, such as main memory of a computer platform described herein. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 101 can include or be in communication with an electronic display 135 that comprises a user interface (UI) 140 for providing, for example, a nucleic acid sequence, an enriched nucleic acid sample data, a protein profile, an expression profile, and an analysis of a RNA expression profile. Examples of UIs include, without limitation, a graphical user interface (GUI) and web-based user interface.

Methods and systems of the present disclosure may be implemented by way of one or more algorithms. An algorithm may be implemented by way of software upon execution by the central processing unit 105. The algorithm can, for example, store, process, identify, or interpret patient data, biological data, biological sequences, reference sequences, and protein profiles.

In some examples, the subject matter disclosed herein can include at least one computer program or use of the same. A computer program can be a sequence of instructions, executable in the digital processing device's CPU, GPU, or TPU, written to perform a specified task. Computer-readable instructions may be implemented as program modules, such as functions, objects, Application Programming Interfaces (APIs), data structures, and the like, that perform particular tasks or implement particular abstract data types. In light of the disclosure provided herein, a computer program may be written in various versions of various languages.

The functionality of the computer-readable instructions may be combined or distributed as desired in various environments. In some examples, a computer program can include one sequence of instructions. In some examples, a computer program can include a plurality of sequences of instructions. In some examples, a computer program may be provided from one location. In some examples, a computer program may be provided from a plurality of locations. In some examples, a computer program can include one or more software modules. In some examples, a computer program can include, in part or in whole, one or more web applications, one or more mobile applications, one or more standalone applications, one or more web browser plug-ins, extensions, add-ins, or add-ons, or combinations thereof.

In some examples, the computer processing may be a method of statistics, mathematics, biology, or any combination thereof. In some examples, the computer processing method comprises a dimension reduction method including, for example, logistic regression, dimension reduction, principal component analysis, autoencoders, singular value decomposition, Fourier bases, singular value decomposition, wavelets, discriminant analysis, support vector machine, tree-based methods, random forest, gradient boost tree, logistic regression, matrix factorization, network clustering, and neural network.

In some examples, the computer processing method is a supervised machine learning method including, for example, a regression, support vector machine, tree-based method, and network.

In some examples, the computer processing method is an unsupervised machine learning method including, for example, clustering, network, principal component analysis, and matrix factorization.

F. Databases

In some examples, the subject matter disclosed herein can include one or more databases, or use of the same to store patient data, biological data, biological sequences, reference sequences, or protein profiles. Reference sequences may be derived from a database. In view of the disclosure provided herein, many databases may be suitable for storage and retrieval of the sequence information. In some examples, suitable databases can include, for example, relational databases, non-relational databases, object-oriented databases, object databases, entity-relationship model databases, associative databases, and XML databases. In some examples, a database may be internet-based. In some examples, a database may be web-based. In some examples, a database may be cloud computing-based. In some examples, a database may be based on one or more local computer storage devices.

In an aspect, the present disclosure provides a non-transitory computer-readable medium comprising instructions that direct a processor to carry out a method disclosed herein.

In an aspect, the present disclosure provides a computing device comprising the computer-readable medium.

In another aspect, the present disclosure provides a system for performing classifications of biological samples comprising:
  a) a receiver to receive a plurality of training samples, each of the plurality of training samples having a plurality of classes of molecules, wherein each of the plurality of training samples comprises one or more known labels;
  b) a feature module to identify a set of features corresponding to an assay that are operable to be computer-processed using the machine learning model for each of the plurality of training samples, wherein the set of features correspond to properties of molecules in the plurality of training samples, wherein for each of the plurality of training samples, the system is operable to subject a plurality of classes of molecules in the training sample to a plurality of different assays to obtain sets of measured values, wherein each set of measured values is from one assay applied to a class of molecules in the training sample, wherein a plurality of sets of measured values are obtained for the plurality of training samples;
  c) an analysis module to analyze the sets of measured values to obtain a training vector for the training sample, wherein the training vector comprises feature values of the N set of features of the corresponding assay, each feature value corresponding to a feature and including one or more measured values, wherein the training vector is formed using at least one feature from at least two of the N sets of features corresponding to a first subset of the plurality of different assays;
  d) a labeling module to inform the system on the training vectors using parameters of the machine learning model to obtain output labels for the plurality of training samples;
  e) a comparator module to compare the output labels to the known labels of the training samples;
  f) a training module to iteratively search for optimal values of the parameters as part of training the machine learning model based on the comparing of the output labels to the known labels of the training samples; and
  g) an output module to provide the parameters of the machine learning model and the set of features for the machine learning model.

Methods of Classifying Subjects in a Population

The disclosed methods are directed to ascertaining parameters of protein expression associated with colon cell proliferative disorders via analysis of expressed proteins in a subject. The method is for use in the improved diagnosis, treatment, and monitoring of colon cell proliferative disorders, more specifically by enabling the improved identification of and differentiation between stages or subclasses of said disorder and the genetic predisposition to said disorders.

In some embodiments, the method comprises analyzing differential expression of proteins in a biological sample from a subject in a population.

The present disclosure provides a method for detecting a colon cell proliferative disorder that may be applied to cell-free samples, e.g., to detect the presence and characteristics of proteins between subjects with and without a colon cell proliferative disorder or between different colon cell proliferative disorders. The method utilizes detection of proteins as the basic "positive" or "negative" for a colon cell proliferative disorder signal compared to a healthy subject not having a colon cell proliferative disorder.

In some embodiments, the colon cell proliferative disorder is selected from the group consisting of adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas.

In one aspect, the present disclosure provides a method for determining a protein profile of a biological sample from a subject comprising:
a) obtaining a biological sample containing proteins from a subject; and
b) measuring in the biological sample the presence and amount of a predetermined panel of at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA to provide a protein profile of the subject.

In some embodiments, the protein profile is associated with a colon cell proliferative disorder and provides classification of a subject as having a colon cell proliferative disorder.

In some embodiments, the biological sample from the subject is selected from the group consisting of bodily fluids, stool, colonic effluent, urine, blood plasma, blood serum, whole blood, isolated blood cells, cells isolated from the blood, and a combination thereof.

In some embodiments, the colon cell proliferative disorder is selected from the group consisting of: adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas.

In some embodiments, the colon cell proliferative disorder is selected from the group consisting of: stage 1 colorectal cancer, stage 2 colorectal cancer, stage 3 colorectal cancer, and stage 4 colorectal cancer.

In some embodiments, the advanced adenoma is a tubular adenoma, a tubulovillous adenoma, a villous adenoma, an adenocarcinoma, or a hyperplastic polyp.

In another aspect, the present disclosure provides a method for detecting a colon cell proliferative disorder in a subject, comprising:
a) obtaining a biological sample containing proteins from a subject;
b) measuring in the biological sample the presence and amount of a predetermined panel of at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA to provide a protein profile of the subject; and
c) computer-processing the protein profile into a machine learning model trained to be capable of distinguishing between healthy subjects and subjects with a colon cell proliferative disorder to provide an output value associated with presence or absence of the colon cell proliferative disorder, thereby indicating the presence or absence of the colon cell proliferative disorder in the subject.

In some embodiments, the biological sample from the subject is selected from the group consisting of bodily fluids, stool, colonic effluent, urine, blood plasma, blood serum, whole blood, isolated blood cells, cells isolated from the blood, and combinations thereof.

In another aspect, disclosed herein is a method for the detection of a protein to generate a protein profile in a sample which comprises:
a) obtaining a biological sample containing proteins from a subject; and
b) measuring in the biological sample the presence and amount of a predetermined panel of at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA to provide a protein profile of the biological sample.

In another aspect, disclosed herein is a method of obtaining data in a biological sample from a subject which comprises detecting at least 6 proteins, wherein said at least 6 proteins are selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA; and, if desired, determining the level of said at least 6 proteins in said sample.

In some embodiments, the colon cell proliferative disorder is selected from the group consisting of: adenoma (adenomatous polyps), polyposis disorder, Lynch syndrome, sessile serrated adenoma (SSA), advanced adenoma, colorectal dysplasia, colorectal adenoma, colorectal cancer, colon cancer, rectal cancer, colorectal carcinoma, colorectal adenocarcinoma, carcinoid tumors, gastrointestinal carcinoid tumors, gastrointestinal stromal tumors (GISTs), lymphomas, and sarcomas.

In some embodiments, the colon cell proliferative disorder is selected from the group consisting of: stage 1 colorectal cancer, stage 2 colorectal cancer, stage 3 colorectal cancer, and stage 4 colorectal cancer.

In another aspect, the present disclosure provides a method for determining a protein profile of a biological sample from a subject comprising:
 a) obtaining a biological sample containing proteins from a subject; and
 b) measuring in the biological sample the presence and amount of a predetermined panel of at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA to provide a protein profile of the subject, thereby determining the protein profile of the subject.

In some embodiments, the predetermined panel of proteins comprises FLT3L, CEACAM5, IL-6RA, ORM, or any combination thereof.

In some embodiments, the predetermined panel of proteins comprises FLT3L, CEACAM5, IL-6RA, ORM, IL-8, AGP, IL-1RT2, TNC, GDF-15, or any combination thereof.

In some embodiments, the predetermined panel of proteins comprises FLT3L, CEACAM5, IL-6RA, ORM, IL-8, AGP, IL-1RT2, TNC, GDF-15, AGRP, Haptoglobin, ANGPTL4, FGF-23, Complement component C2, ORM2, FGF-23, MUC-16, EGF, or any combination thereof.

In some embodiments, the panel comprises FLT3L, CEACAM5, IL-6, IL-8, MIP-3a, IL-1RT2, TNC, or a combination thereof.

In some embodiments, the panel comprises FLT3L, CEACAM5, IL-6, IL-8, MIP-3a, IL-1RT2, TNC, HGFR, THBS2, CA125 (MUC-16), CA19-9, CA15-3 (MUC-1), or a combination thereof.

In some embodiments, the panel comprises total PSA.

In another aspect, the present disclosure provides a method for detecting a colon cell proliferative disorder in a subject, comprising:
 a) obtaining a biological sample containing proteins from a subject;
 b) measuring in the biological sample the presence and amount of a predetermined panel of at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA to provide a protein profile of the subject; and
 c) computer-processing the protein profile of the subject into a machine learning model trained to distinguish between subjects not having the colon cell proliferative disorder and subjects having the colon cell proliferative disorder; and
 d) outputting by the machine learning model based on the protein profile a value associated with subjects having the colon cell proliferative disorder, thereby detecting the colon cell proliferative disorder in the subject.

In another aspect, the present disclosure provides a method for monitoring minimal residual disease in a subject previously treated for disease comprising: determining a protein profile of a biological sample from the subject using a predetermined panel of proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA, thereby generating a baseline protein state; and determining a protein profile of a biological sample from the subject at one or more time points after the generating of the baseline protein state, thereby generating a current protein state, wherein a change between the baseline protein state and the current protein state indicates a change in the minimal residual disease in the subject.

In some embodiments, the minimal residual disease is selected from the group consisting of response to treatment, tumor load, residual tumor post-surgery, relapse, secondary screen, primary screen, and cancer progression.

The trained machine learning methods, models, and discriminate classifiers described herein may be applied toward various medical applications including cancer detection, diagnosis, and treatment responsiveness. As models may be trained with subject metadata and analyte-derived features, the applications may be tailored to stratify subjects in a population and guide treatment decisions accordingly.

Diagnosis

Methods and systems provided herein may perform predictive analytics using artificial intelligence-based approaches to analyze acquired data from a subject (patient) to generate an output of diagnosis of the subject having cancer (e.g., colorectal cancer). For example, the application may apply a prediction algorithm to the acquired data to generate the diagnosis of the subject having the cancer. The prediction algorithm may comprise an artificial intelligence-based predictor, such as a machine learning-based predictor, configured to process the acquired data to generate the diagnosis of the subject having the cancer.

The machine learning predictor may be trained using datasets, e.g., datasets generated by performing protein assays using the signature panels described herein on biological samples of subjects from one or more sets of cohorts of patients having cancer as inputs and known diagnosis (e.g., staging and/or tumor fraction) outcomes of the subjects as outputs to the machine learning predictor.

Training datasets (e.g., datasets generated by performing assays using the signature panels described herein on biological samples of subjects) may be generated from, for example, one or more sets of subjects having common characteristics (features) and outcomes (labels). Training datasets may comprise a set of features and labels corresponding to the features relating to diagnosis. Features may comprise characteristics such as, for example, certain ranges or categories of protein assay measurements, such as the presence or characteristics of one or more proteins in a biological sample from a healthy subject and diseased subject. For example, a set of features collected from a given subject at a given time point may collectively serve as a diagnostic signature, which may be indicative of an identified cancer of the subject at the given time point. Characteristics may also include labels indicating the subject's diagnostic outcome, such as for one or more cancers.

Labels may comprise outcomes such as, for example, a known diagnosis (e.g., staging and/or tumor fraction) outcomes of the subject. Outcomes may include a characteristic associated with the cancers in the subject. For example, characteristics may be indicative of the subject having one or more cancers.

Training sets (e.g., training datasets) may be selected by random sampling of a set of data corresponding to one or more sets of subjects (e.g., retrospective and/or prospective cohorts of patients having or not having one or more cancers). Alternatively, training sets (e.g., training datasets) may be selected by proportionate sampling of a set of data corresponding to one or more sets of subjects (e.g., retrospective and/or prospective cohorts of patients having or not having one or more cancers). Training sets may be balanced across sets of data corresponding to one or more sets of subjects (e.g., patients from different clinical sites or trials). The machine learning predictor may be trained until certain predetermined conditions for accuracy or performance are satisfied, such as having minimum desired values corresponding to diagnostic accuracy measures. For example, the diagnostic accuracy measure may correspond to prediction of a diagnosis, staging, or tumor fraction of one or more cancers in the subject.

Examples of diagnostic accuracy measures may include sensitivity, specificity, positive predictive value (PPV), negative predictive value (NPV), accuracy, and area under the curve (AUC) of a Receiver Operating Characteristic (ROC) curve corresponding to the diagnostic accuracy of detecting or predicting the cancer (e.g., colorectal cancer).

In an aspect, the disclosure provides a method of using a classifier capable of distinguishing a population of subjects comprising:
 a) obtaining a biological sample containing proteins from a subject;
 b) measuring in the biological sample the presence and amount of a predetermined panel of at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA, thereby providing a protein profile of the subject;
 c) computer-processing the protein profile of the subject into a machine learning model trained to distinguish in two or more populations; and
 d) outputting by the machine learning model based on the protein profile a value associated with the populations, thereby distinguishing a population of subjects.

In some embodiments, the predetermined panel of proteins comprises FLT3L, CEACAM5, IL-6RA, ORM, or any combination thereof.

In some embodiments, the predetermined panel of proteins comprises FLT3L, CEACAM5, IL-6RA, ORM, IL-8, AGP, IL-1RT2, TNC, GDF-15, or any combination thereof.

In some embodiments, the predetermined panel of proteins comprises FLT3L, CEACAM5, IL-6RA, ORM, IL-8, AGP, IL-1RT2, TNC, GDF-15, AGRP, Haptoglobin, ANGPTL4, FGF-23, Complement C2, ORM2, FGF-23, MUC-16, EGF, or any combination thereof.

In some embodiments, the panel comprises FLT3L, CEACAM5, IL-6, IL-8, MIP-3a, IL-1RT2, TNC or a combination thereof.

In some embodiments, the panel comprises FLT3L, CEACAM5, IL-6, IL-8, MIP-3a, IL-1RT2, TNC, HGFR, THBS2, CA125 (MUC-16), CA19-9, CA15-3 (MUC-1), or a combination thereof.

In some embodiments, the panel comprises total PSA.

In another aspect, the present disclosure provides a method for identifying a cancer in a subject, comprising:
 a) obtaining a biological sample containing proteins from a subject;
 b) measuring in the biological sample the presence and amount of a predetermined panel of at least 6 proteins selected from the group consisting of: EGF, FGF-2, FLT3L, Fractalkine, IL-1a, IL-2, IL-6, IL-8, GROa, MIP-3a, Complement component C2, Complement component C9, Factor D, Factor I, MBL, MMP-2, GDF-15, Osteonectin, Periostin, ANGPTL4, FGF-21, FGF-23, HGF, Angiopoietin-2, BMP-9, IL-1RII, HGFR, IL-6ra, OPN, Tenascin-C, Thrombospondin-2, uPAR, CD44, Kallikrein-6, Mesothelin, EpCAM, Apo A1, AGP, A2 MB, Fetuin A, HP, L-Selectin, Complement component C1q, Complement component C3, Complement component C3b, Factor B, Factor H, Properdin, AGRP, MMP-12, CYFRA21-1, HE4, total PSA, MIF, AFP, CA125, CA19-9, CA15-3 (MUC-1), and CEA, thereby providing a protein profile of the subject;

c) computer-processing the protein profile into a machine learning model trained to be capable of distinguishing between healthy subjects and subjects with a colon cell proliferative disorder to provide an output value associated with presence or absence of the colon cell proliferative disorder, thereby indicating the presence or absence of the colon cell proliferative disorder in the subject to generate a likelihood of said subject having said cancer.

In some embodiments, the predetermined panel of proteins comprises FLT3L, CEACAM5, IL-6RA, ORM, or any combination thereof.

In some embodiments, the predetermined panel of proteins comprises FLT3L, CEACAM5, IL-6RA, ORM, IL-8, AGP, IL-1RT2, TNC, GDF-15, or any combination thereof.

In some embodiments, the predetermined panel of proteins comprises FLT3L, CEACAM5, IL-6RA, ORM, IL-8, AGP, IL-1RT2, TNC, GDF-15, AGRP, Haptoglobin, ANGPTL4, FGF-23, Complement component C2, ORM2, FGF-23, MUC-16, EGF, or any combination thereof.

In some embodiments, the panel comprises FLT3L, CEACAM5, IL-6, IL-8, MIP-3a, IL-1RT2, TNC or a combination thereof.

In some embodiments, the panel comprises FLT3L, CEACAM5, IL-6, IL-8, MIP-3a, IL-1RT2, TNC, HGFR, THBS2, CA125 (MUC-16), CA19-9, CA15-3 (MUC-1), or a combination thereof.

In some embodiments, the panel comprises total PSA.

A variety of statistical and mathematical methods for establishing the threshold or cutoff level of expression may be used. A threshold or cutoff expression level for a particular biomarker may be selected, for example, based on data from Receiver Operating Characteristic (ROC) plots, as described in the Examples and Figures disclosed herein. One of skill in the art will appreciate that these threshold or cutoff expression levels can be varied, for example, by moving along the ROC plot for a particular biomarker or combinations thereof, to obtain different values for sensitivity or specificity thereby affecting overall assay performance. For example, if the objective is to have a robust diagnostic method from a clinical point of view, high sensitivity should be prioritized. However, if the goal is to have a cost-effective method, high specificity should be prioritized. The best cutoff refers to the value obtained from the ROC plot for a particular biomarker that produces the best sensitivity and specificity. Sensitivity and specificity values are calculated over the range of thresholds (cutoffs). Thus, the threshold or cutoff values can be selected such that the sensitivity and/or specificity are at least about 50%, and can be, for example, at least 55%, at least 60%, at least 65%, at least 70%, at least 75%, at least 80%, at least 85%, at least 90%, at least 95%, at least 96%, at least 97%, at least 98%, at least 99% or at least 100% in at least 60%, at least 65%, at least 70%, at least 75%, or at least 80% of the patient population assayed.

Consequently, some embodiments of the present disclosure are carried out by determining the presence and/or levels of at least the proteins previously cited in a minimally-invasive sample isolated from the subject to be diagnosed or screened, and comparing the presence and/or levels of the proteins with predetermined threshold or cutoff values, wherein the predetermined threshold or cutoff values correspond to the expression level of said proteins which correlates with the highest specificity at a desired sensitivity in a ROC curve calculated based on the expression levels of the proteins determined in a patient population being at risk of suffering colorectal cancer or colorectal adenoma, wherein the overexpression of at least one of said proteins with respect to said predetermined cutoff value is indicative that the subject suffers from colorectal cancer or colorectal adenoma with said desired sensitivity.

As another example, such a predetermined condition may be that the specificity of predicting the colon cell proliferative disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the positive predictive value (PPV) of predicting the colon cell proliferative disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the negative predictive value (NPV) of predicting the colon cell proliferative disorder comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the area under the curve (AUC) of a Receiver Operating Characteristic (ROC) curve of predicting the colon cell proliferative disorder comprises a value of at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

Monitoring Colorectal Cancer

After using a trained algorithm to process the dataset, the colorectal cancer may be identified or monitored in the subject. The identification may be based at least in part on quantitative measures of proteins of the dataset at a panel of colorectal cancer-associated proteins. For example, the monitoring may comprise assessing the colorectal cancer of the subject at each of two or more different time points.

In some embodiments, methods disclosed herein may be applied to monitor and/or predict tumor load.

In some embodiments, methods disclosed herein may be applied to detect and/or predict residual tumor post-surgery.

In some embodiments, methods disclosed herein may be applied to detect and/or predict minimal residual disease post-treatment.

In some embodiments, methods disclosed herein may be applied to detect and/or predict relapse.

In an aspect, methods disclosed herein may be applied as a secondary screen.

In an aspect, methods disclosed herein may be applied as a primary screen.

In an aspect, methods disclosed herein may be applied to monitor cancer development.

In an aspect, methods disclosed herein may be applied to monitor and/or predict cancer risk.

The colorectal cancer may be identified in the subject at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The accuracy of identifying the colorectal cancer by the trained algorithm may be calculated as the percentage of independent test samples (e.g., subjects known to have the colorectal cancer or subjects with negative clinical test results for the colorectal cancer) that are correctly identified or classified as having or not having the colorectal cancer.

The colorectal cancer may be identified in the subject with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the colorectal cancer using the trained algorithm may be calculated as the percentage of cell-free biological samples identified or classified as having the colorectal cancer that correspond to subjects that truly have the colorectal cancer.

The colorectal cancer may be identified in the subject with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the colorectal cancer using the trained algorithm may be calculated as the percentage of cell-free biological samples identified or classified as not having the colorectal cancer that correspond to subjects that truly do not have the colorectal cancer.

The colorectal cancer may be identified in the subject with a clinical sensitivity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the colorectal cancer using the trained algorithm may be calculated as the percentage of independent test samples associated with presence of the colorectal cancer (e.g., subjects known to have the colorectal cancer) that are correctly identified or classified as having the colorectal cancer.

The colorectal cancer may be identified in the subject with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the colorectal cancer using the trained algorithm may be calculated as the percentage of independent test samples associated with absence of the colorectal cancer (e.g., subjects with negative clinical test results for the colorectal cancer) that are correctly identified or classified as not having the colorectal cancer.

In some embodiments, the trained algorithm may determine that the subject is at risk of colorectal cancer of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

The trained algorithm may determine that the subject is at risk of colorectal cancer at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more.

Upon identifying the subject as having the colorectal cancer, the subject may be optionally provided with a therapeutic intervention (e.g., prescribing an appropriate course of treatment to treat the colorectal cancer of the subject). The therapeutic intervention may comprise a prescription of an effective dose of a drug, a further testing or evaluation of the colorectal cancer, a further monitoring of the colorectal cancer, or a combination thereof. If the subject is currently being treated for the colorectal cancer with a course of treatment, the therapeutic intervention may comprise a subsequent different course of treatment (e.g., to increase treatment efficacy due to non-efficacy of the current course of treatment).

The therapeutic intervention may comprise recommending the subject for a secondary clinical test to confirm a diagnosis of the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

The colorectal cancer of the subject may be monitored by monitoring a course of treatment for treating the colorectal cancer of the subject. The monitoring may comprise assessing the colorectal cancer of the subject at two or more time points. The assessing may be based at least on the quantitative measures of proteins of the dataset at a panel of colorectal cancer-associated proteins comprising quantitative measures of a panel of colorectal cancer-associated proteins determined at each of the two or more time points.

In some embodiments, a difference in the quantitative measures of proteins of the dataset at a panel of colorectal cancer-associated proteins comprising quantitative measures of a panel of colorectal cancer-associated proteins determined between the two or more time points may be indicative of one or more clinical indications, such as (i) a diagnosis of the colorectal cancer of the subject, (ii) a prognosis of the colorectal cancer of the subject, (iii) an increased risk of the colorectal cancer of the subject, (iv) a decreased risk of the colorectal cancer of the subject, (v) an efficacy of the course of treatment for treating the colorectal cancer of the subject, and (vi) a non-efficacy of the course of treatment for treating the colorectal cancer of the subject.

In some embodiments, a difference in the quantitative measures of proteins comprising quantitative measures of a panel of colorectal cancer-associated proteins determined between the two or more time points may be indicative of a diagnosis of the colorectal cancer of the subject. For example, if the colorectal cancer was not detected in the subject at an earlier time point but was detected in the subject at a later time point, then the difference is indicative of a diagnosis of the colorectal cancer of the subject. A clinical action or decision may be made based on this indication of diagnosis of the colorectal cancer of the subject, such as, for example, prescribing a new therapeutic intervention for the subject. The clinical action or decision may comprise recommending the subject for a secondary clinical test to confirm the diagnosis of the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

In some embodiments, a difference in the quantitative measures of proteins of the dataset at a panel of colorectal cancer-associated proteins comprising quantitative measures of a panel of colorectal cancer-associated proteins determined between the two or more time points may be indicative of a prognosis of the colorectal cancer of the subject.

In some embodiments, a difference in the quantitative measures of proteins of the dataset at a panel of colorectal cancer-associated proteins comprising quantitative measures of a panel of colorectal cancer-associated proteins determined between the two or more time points may be indicative of the subject having an increased risk of the colorectal cancer. For example, if the colorectal cancer was detected in the subject both at an earlier time point and at a later time point, and if the difference is a positive difference (e.g., the quantitative measures of proteins of the dataset at a panel of colorectal cancer-associated proteins increased from the earlier time point to the later time point), then the difference may be indicative of the subject having an increased risk of the colorectal cancer. A clinical action or decision may be made based on this indication of the increased risk of the colorectal cancer, e.g., prescribing a new therapeutic intervention or switching therapeutic interventions (e.g., ending a current treatment and prescribing a new treatment) for the subject. The clinical action or decision may comprise recommending the subject for a secondary clinical test to confirm the increased risk of the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

In some embodiments, a difference in the quantitative measures of proteins of the dataset at a panel of colorectal cancer-associated proteins comprising quantitative measures of a panel of colorectal cancer-associated proteins determined between the two or more time points may be indicative of the subject having a decreased risk of the colorectal cancer. For example, if the colorectal cancer was detected in the subject both at an earlier time point and at a later time point, and if the difference is a negative difference (e.g., the quantitative measures of proteins of the dataset at a panel of colorectal cancer-associated proteins comprising quantitative measures of a panel of colorectal cancer-associated proteins decreased from the earlier time point to the later time point), then the difference may be indicative of the subject having a decreased risk of the colorectal cancer. A clinical action or decision may be made based on this indication of the decreased risk of the colorectal cancer (e.g., continuing or ending a current therapeutic intervention) for the subject. The clinical action or decision may comprise recommending the subject for a secondary clinical test to confirm the decreased risk of the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

In some embodiments, a difference in the quantitative measures of proteins of the dataset at a panel of colorectal cancer-associated proteins comprising quantitative measures of a panel of colorectal cancer-associated proteins determined between the two or more time points may be indicative of an efficacy of the course of treatment for treating the colorectal cancer of the subject. For example, if the colorectal cancer was detected in the subject at an earlier time point but was not detected in the subject at a later time point, then the difference may be indicative of an efficacy of the course of treatment for treating the colorectal cancer of the subject. A clinical action or decision may be made based on this indication of the efficacy of the course of treatment for treating the colorectal cancer of the subject, e.g., continuing or ending a current therapeutic intervention for the subject. The clinical action or decision may comprise recommending the subject for a secondary clinical test to confirm the efficacy of the course of treatment for treating the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

In some embodiments, a difference in the quantitative measures of proteins of the dataset at a panel of colorectal cancer-associated proteins comprising quantitative measures of a panel of colorectal cancer-associated proteins determined between the two or more time points may be indicative of a non-efficacy of the course of treatment for treating the colorectal cancer of the subject. For example, if the colorectal cancer was detected in the subject both at an earlier time point and at a later time point, and if the difference is a positive or zero difference (e.g., the quantitative measures of proteins of the dataset at a panel of colorectal cancer-associated proteins comprising quantitative measures of a panel of colorectal cancer-associated proteins increased or remained at a constant level from the earlier time point to the later time point), and if an efficacious treatment was indicated at an earlier time point, then the difference may be indicative of a non-efficacy of the course of treatment for treating the colorectal cancer of the subject. A clinical action or decision may be made based on this indication of the non-efficacy of the course of treatment for treating the colorectal cancer of the subject, e.g., ending a current therapeutic intervention and/or switching to (e.g., prescribing) a different new therapeutic intervention for the subject. The clinical action or decision may comprise recommending the subject for a secondary clinical test to confirm the non-efficacy of the course of treatment for treating the colorectal cancer. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cell-free biological cytology, a FIT test, an FOBT test, or any combination thereof.

Kits

The present disclosure provides kits for identifying or monitoring a cancer of a subject. A kit may comprise antibodies, probes, or primers for identifying a quantitative measure (e.g., indicative of a presence, absence, or relative amount) of proteins at each of a plurality of cancer-associated proteins in a cell-free biological sample of the subject. A quantitative measure (e.g., indicative of a presence, absence, or relative amount) of a panel of proteins in the cell-free biological sample may be indicative of one or more cancers. The probes may be selective for the proteins in the cell-free biological sample. A kit may comprise instructions for using the probes to process the cell-free biological sample to generate datasets indicative of a quantitative measure (e.g., indicative of a presence, absence, or relative amount) of proteins in a cell-free biological sample of the subject.

The probes in the kit may be selective for the proteins or sequences encoding the proteins at the plurality of cancer-associated proteins in the cell-free biological sample. The probes in the kit may be configured to selectively enrich protein molecules corresponding to the plurality of cancer-associated proteins. The probes in the kit may be antibodies recognized by the proteins and tagged to permit isolation after binding to the proteins in the biological sample.

The instructions in the kit may comprise instructions to assay the cell-free biological sample using the probes that are selective for the cancer-associated proteins in the cell-free biological sample. A quantitative measure (e.g., indicative of a presence, absence, or relative amount) of proteins or sequences encoding the proteins at each of a plurality of cancer-associated proteins in the cell-free biological sample may be indicative of one or more cancers.

The instructions in the kit may comprise instructions to measure and interpret assay readouts, which may be quantified at one or more of the plurality of cancer-associated proteins to generate the datasets indicative of a quantitative measure (e.g., indicative of a presence, absence, or relative amount) of proteins or sequences encoding the proteins at each of the plurality of cancer-associated proteins in the cell-free biological sample.

EXAMPLES

Example 1: Protein Analysis in Patient Plasma Samples

In cancer, proteins, whether cancer neoantigens or canonical proteins, represent a source of potential early diagnostic biomarkers for colorectal cancer. Protein features can be determined from plasma by evaluating protein overexpression, depletion, or mutations in cancer patients. Some proteins have been identified to be associated with breast, prostate, colorectal, lung, and ovarian cancers.

To identify proteins that are informative for the methods and classifiers described herein, plasma from patients with colon cell proliferative disorders and plasma of subjects without colon cell proliferative disorders (control plasma or reference plasma) have been examined to identify a signature panel of proteins produced by patients having a colon cell proliferative disorder in response to the colon cell proliferative disorder and respective reactive proteins. To that end, plasma from patients with colon cell proliferative disorders and control plasma were profiled using both mass spectrometry based proteomics and immunoaffinity assays to identify and quantify circulating plasma proteins. Plasma may or may not have been depleted of high abundant proteins (e.g., albumin, immunoglobulins) prior to characterization.

The protein panel identified by this analysis allowed differentiation between plasma from subjects with a colon cell proliferative disorder and healthy subjects.

Methods

Sample Categorization

To detect proteins in a plasma sample, immunoassays and mass spectrometry assays were executed with plasma drawn from subjects subsequently identified as having colorectal cancer (CRC), advanced adenoma (AA), benign polyp (NAA), or none of these (NEG).

Plasma were obtained using a standardized blood collection and processing protocol, and subsequently stored at −80° C. until use. Written consent was obtained from all subjects under institutional review board approval.

A description of the study cohort is provided in TABLE 1, which shows the number of healthy and cancer samples used for CRC experiments in the classification model (by gender and age).

TABLE 1

|  |  | CRC (n = 105) | AA (n = 137) | NAA (n = 164) | Control/NEG (n = 583) |
|---|---|---|---|---|---|
| Gender | Female 360 (44.4%) | 38 | 61 | 70 | 273 |
|  | Male 451 (55.6%) | 67 | 76 | 94 | 310 |
| Age | Median, IQR | Median age: 65.0 IQR: 56.0-72.0 | Median age: 63.0 IQR: 55.5-70.0 | Median age: 65.5 IQR: 62.0-69.0 | Median age: 62.0 IQR: 46.0-67.0 |

The primary goal of this study was to identify serum protein biomarkers that would distinguish colorectal cancer from advanced adenoma, benign disease, and healthy controls to improve the sensitivity of current biomarkers and guide clinical decisions.

Plasma was isolated from subject samples representing NEG, CRC, AA, and NAA subject populations and screened on a protein array. A total of 1,472 features were identified between NEG, CRC, AA, and NAA subject populations, and interrogated for differential expression in plasma from subjects with colon cell proliferative disorder and in healthy subject plasma.

All protein quantification data was normalized and reported in either relative or absolute scale.

Filtering Feature Values:

The ability for each protein to discriminate patients with and without a specific condition was assessed by calculating metrics for the three groups for discrimination. The discrimination groups were: disease negative vs. colorectal cancer (NEG vs. CRC), disease negative vs. advanced adenoma (NEG vs. AA), and disease negative vs. advanced adenoma and non-advanced adenoma (NEG vs. AA+NAA). The metrics calculated for this comparison included Hedges' G effect size metric, Wasserstein distance metric, feature weight in a single assay linear logistic regression with elastic net regularization, feature importance in a single assay nonlinear random forest, and feature weight in a multi-assay logistic regression model.

For each protein, the protein's percentile in the per metric distribution over all proteins was calculated. Proteins were ranked by the percentile in the per metric distribution. Proteins were retained for further consideration if the proteins satisfied at least one of the following criteria:
A) had a maximum metric percentile at 95 or above and for the median metric percentile at 90 or above from the protein-only analysis;
B) was ranked in the top 25 for maximum metric percentile or for median metric percentile; and
C) was ranked in the top 25 by feature weight in a multi-assay logistic regression model.

Some literature derived features were also included for consideration based on an extensive literature search. Features satisfying the above criteria including the literature derived features were further explored for reagent availability and of them the features were selected.

Figure 2:
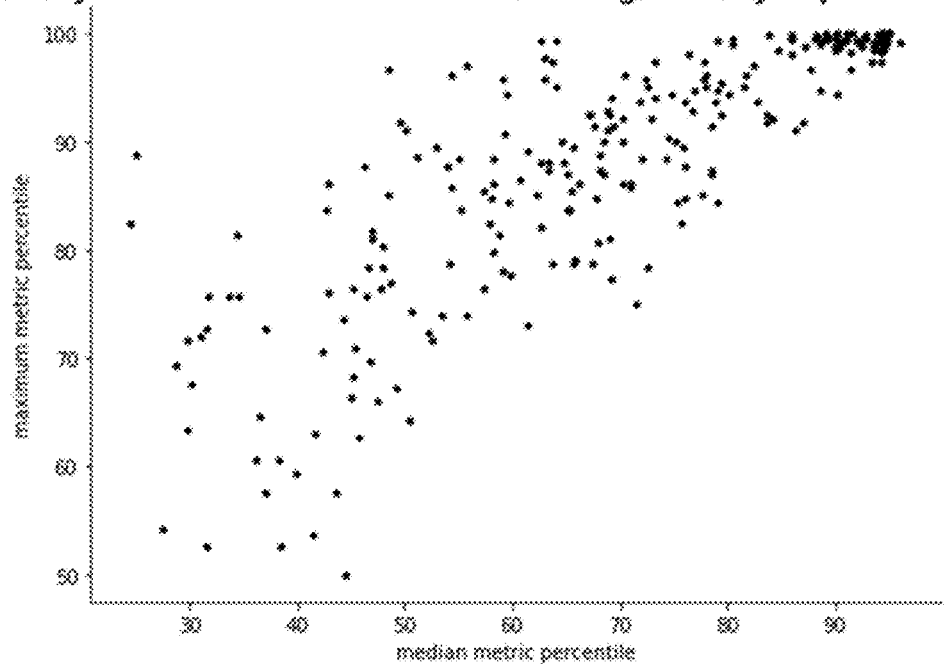
FIG. 2 provides visualization of the per-protein percentiles calculated on the single analyte protein data for all available targets in the protein marker datasets.

FIG. 2 provides visualization of the per-protein percentiles calculated on the single analyte protein data for all available targets in the protein marker datasets.

Figure 3:
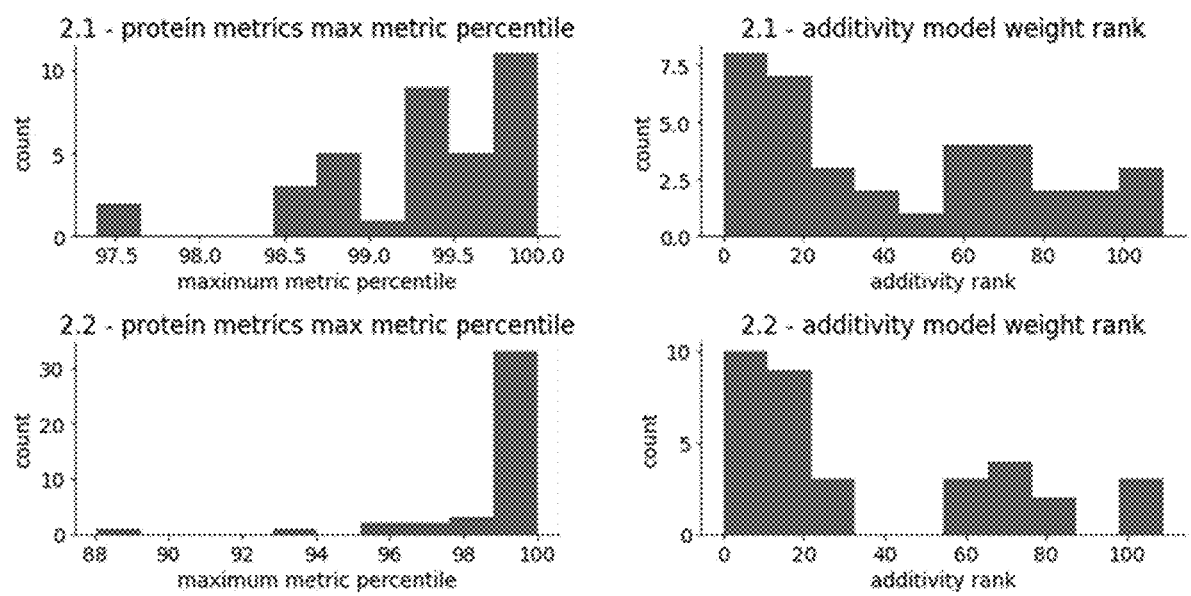
FIG. 3 provides visualization of the metrics from the single assay protein analysis (left panels) and the multi-assay additivity analysis (right panels). The 2.1 list consists of proteins that satisfy two criteria. The first criterion is proteins that satisfy the thresholds for maximum and median percentile metrics. The second criterion is proteins that pass the usage frequency and performance thresholds defined by additivity. The 2.2 list consists of the intersection of proteins found when taking the top 25 proteins by rank for maximum and median percentile metric.
Figure 4:
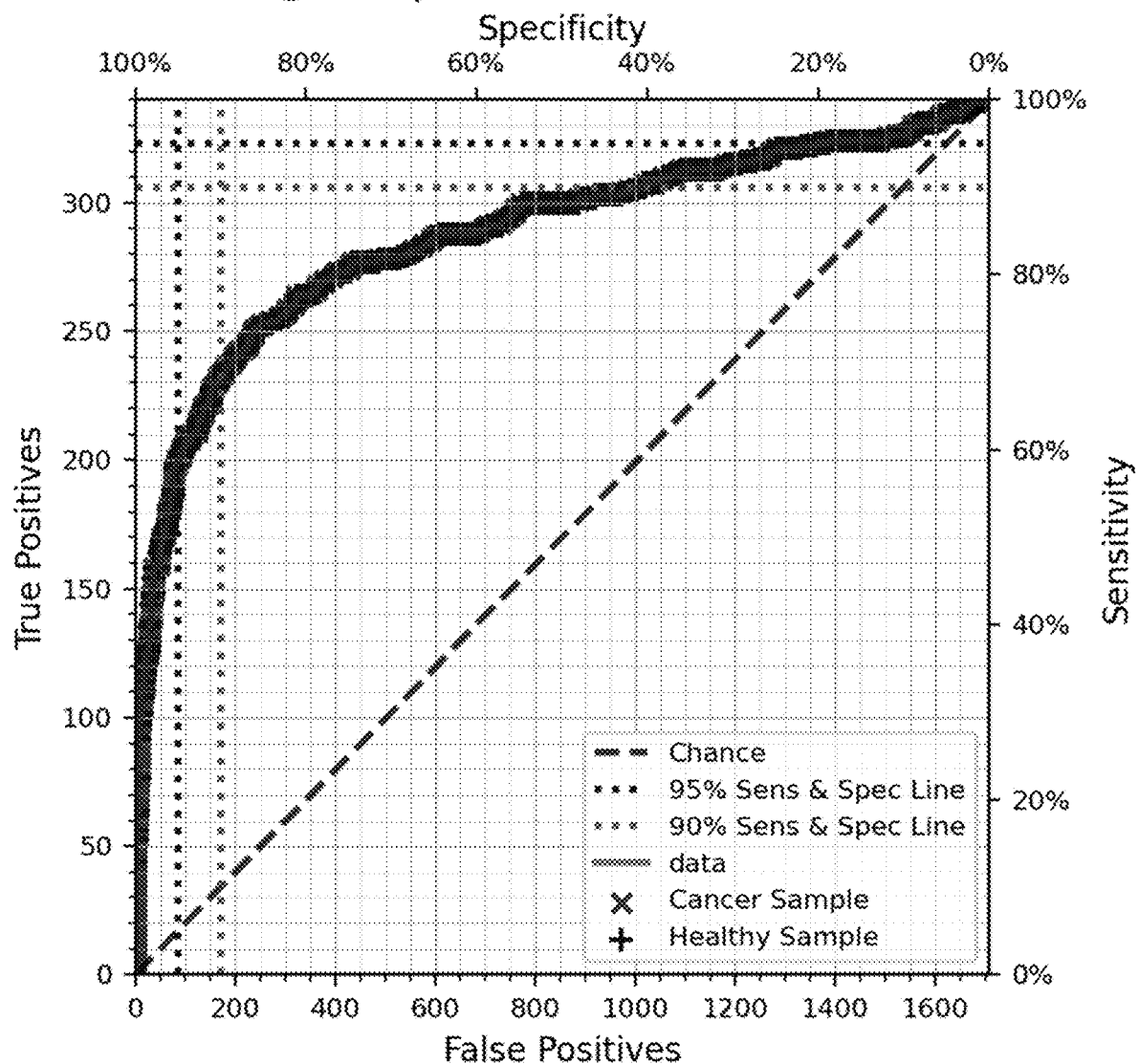
FIG. 4 provides a ROC curve showing classification performance of the 53 features CRC vs. NEG on discovery data where all data were used for feature selection but model weights were defined within cross validation (no true hold-out in this performance).
Figure 5:
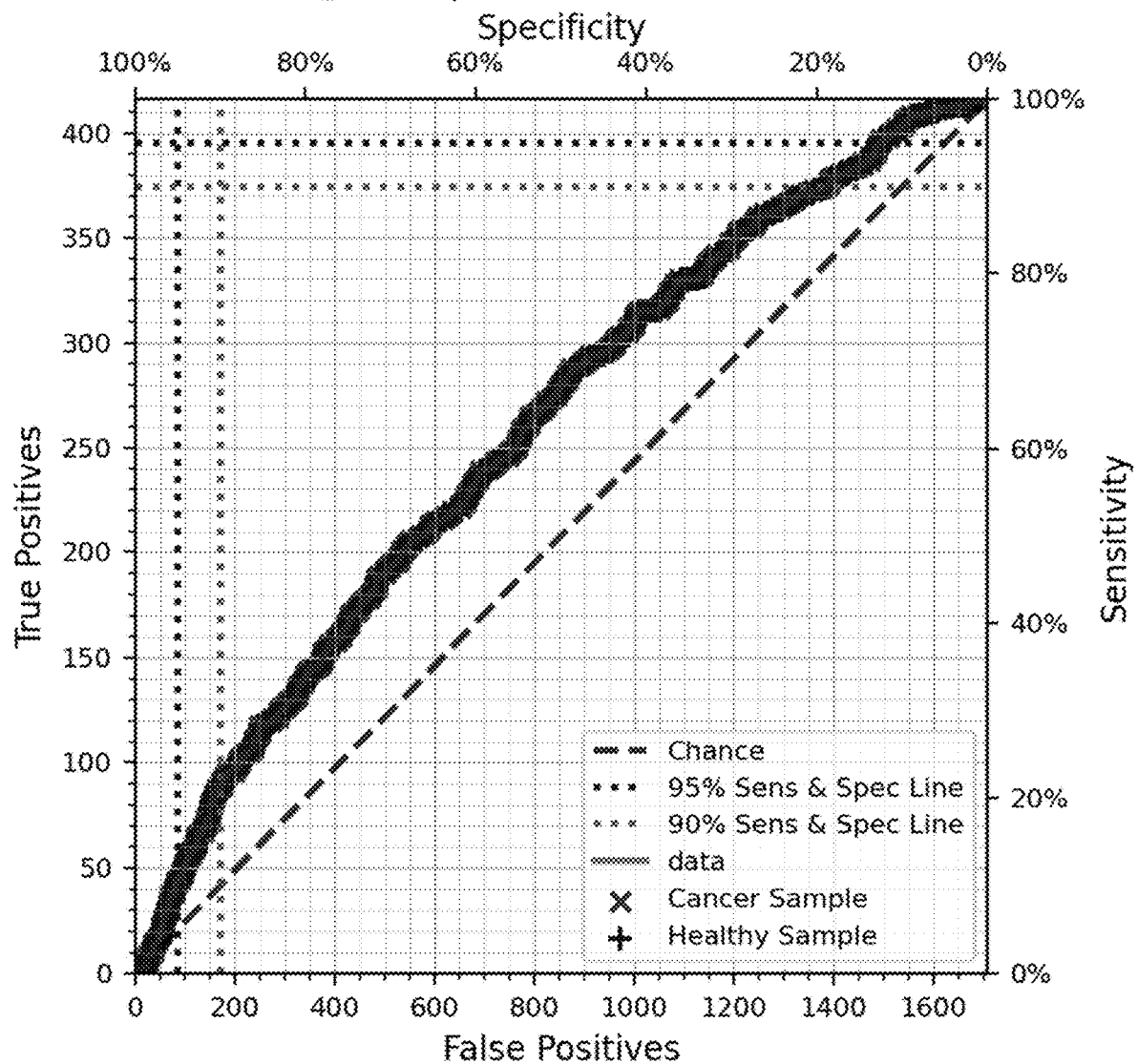
FIG. 5 provides a ROC curve showing classification performance of the 53 features AA vs. NEG on discovery data where all data was used for feature selection but model weights were defined within cross validation (no true hold-out in this performance).

FIG. 3 provides visualization of the metrics from the single assay protein analysis (left panels) and the multi-assay analysis (right panels). The 2.1 list consists of the intersection of proteins found when thresholding the maximum and median percentile metric distributions and intersected that list with the lists that pass the usage frequency and performance thresholds defined by additivity. The 2.2 list consists of the intersection of proteins found when taking the top 25 proteins by rank for maximum and median percentile metric.

Results

NEG, NAA, AA, CRC

TABLE 2 provides a list of identified proteins of a protein biomarker panel for CRC discrimination.

TABLE 2

| EGF | FGF-23 | L-Selectin |
| FGF-2 | HGF | Complement C1q |
| FLT3L | Angiopoietin-2 | C3 |
| Fractalkine | BMP-9 | C3b |
| IL-1a, | IL-1RII | Factor B |
| IL-2 | HGFR | Factor H |
| IL-6 | IL-6ra | Properdin |
| IL-8 | OPN | AGRP |
| GROa | Tenascin-C | MMP-12 |
| MIP-3a | Thrombospondin-2 | CYFRA21-1 |
| Complement component C2 | uPAR | HE4 |
| Complement component C9 | CD44 | total prostate-specific antigen (PSA) |
| Factor D | Kallikrein-6 | MIF |
| MBL | Mesothelin | AFP |
| MMP-2 | EpCAM | CA125 |
| GDF-15 | Apo A1 | CA19-9 |
| Osteonectin | AGP | CEA |
| Periostin | A2MB | Factor I |
| ANGPTL4 | Fetuin A | |
| FGF-21 | HP | |

ROC Cross validation test fold mean metrics. Mean performance metrics were determined across 20 folds of discovery data where all data was used for feature selection, but model weights were defined within cross validation.

For "Target 0.9 Specificity" metrics, predictions were made based on prediction probabilities (scores) and labels. The threshold that maximizes sensitivity while achieving just over 0.9 specificity was selected. For "Empirical" metrics, predictions were made by using the default prediction threshold from the classifier and not targeting any specific specificity or based on test samples. Confidence intervals are reported in square brackets and are the mean of the per-fold confidence intervals.

TABLE 3 provides classification performance specification of the 53 features CRC vs. NEG on discovery data where all data was used for feature selection, but model weights were defined within cross validation (no true hold-out in this performance).

TABLE 3

| AUC [C.I.] | Target 0.9 Specificity | | Empirical | | | | | |
| --- | --- | --- | --- | --- | --- | --- | --- | --- |
| | Sensitivity | Specificity | Sensitivity | Specificity | TP | FN | TN | FP |
| 0.85 [0.718, 0.922] | 0.688 [0.426, 0.882] | 0.906 [0.824, 0.959] | 0.712 [0.45, 0.896] | 0.875 [0.787, 0.936] | 12.1 | 4.9 | 74.75 | 10.65 |

TABLE 4 provides classification performance specification of the 53 features AA vs. NEG on discovery data where all data was used for feature selection, but model weights were defined within cross validation (no true holdout in this performance).

TABLE 4

| AUC [C.I.] | Target 0.9 Specificity | | Empirical | | | | | |
| --- | --- | --- | --- | --- | --- | --- | --- | --- |
| | Sensitivity | Specificity | Sensitivity | Specificity | TP | FN | TN | FP |
| 0.621 [0.483, 0.738] | 0.197 [0.065, 0.422] | 0.906 [0.824, 0.959] | 0.48 [0.264, 0.702] | 0.687 [0.578, 0.783] | 10.0 | 10.8 | 58.65 | 26.75 |

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing an invention of the disclosure. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of detecting a cancer in a subject using a computer specifically programmed to detect the cancer, wherein the cancer comprises a colorectal cancer, wherein the computer is programmed with instructions to perform at least:
   (a) obtaining a protein profile of the subject comprising a measured amount of a protein from a pre-determined protein panel comprising at least six proteins selected from the group consisting of: epidermal growth factor (EGF), fibroblast growth factor 2 (FGF-2), FMS-like tyrosine kinase 3 ligand (FLT3L), Fractalkine, Interleukin-1 alpha (IL-1a), IL-2, IL-6, IL-8, GRO-alpha-MGSA (GROa), Macrophage inflammatory protein-3 alpha (MIP-3a), Complement component C2, Complement component C9, Factor D, Factor I, Mannose-binding lectin (MBL), matrix metalloproteinase-2 (MMP-2), Growth/Differentiation Factor-15 (GDF-15), Osteonectin, Periostin, Angiopoietin-like 4 (ANGPTL4), FGF-21, FGF-23, hepatocyte growth factor (HGF), Angiopoietin-2, Bone Morphogenetic Protein-9 (BMP-9), IL-1RII, hepatocyte growth factor receptor (HGFR), IL-6ra, Osteopontin (OPN), Tenascin-C, Thrombospondin-2, urokinase plasminogen activator surface receptor (uPAR), CD44, Kallikrein-6, Mesothelin, epithelial cellular adhesion molecule (Ep-CAM), Apo A1, alpha-1-acid glycoprotein (AGP), Alpha-2-macroglobulin (A2MB), Fetuin A, haptoglobin (HP), L-Selectin, Complement component C1q, Complement component C3, Complement component C3b, Factor B, Factor H, Properdin, Agouti-Related Protein (AGRP), MMP-12, Cytokeratin-19 fragment 21-1 (CYFRA21-1), Human epididymis protein 4 (HE4), total prostate-specific antigen (PSA), Macrophage migration inhibitory factor (MIF), alpha fetoprotein (AFP), cancer antigen 125 (CA125), CA19-9, CA15-3 (MUC-1), and carcinoembryonic antigen (CEA), in a biological sample obtained or derived from the subject;
   (b) detecting an increased risk of the colorectal cancer in the subject, wherein the detecting comprises processing the protein profile using a trained machine learning model, wherein the trained machine learning model is trained with training data comprising: (i) a first set of biological samples obtained or derived from subjects with advanced adenoma, (ii) a second set of biological samples obtained or derived from control subjects without advanced adenoma, (iii) a third set of biological samples obtained or derived from subjects with benign polyp, and (iv) a fourth set of biological samples obtained or derived from control subjects without benign polyp, to provide an output value indicative of the increased risk of the colorectal cancer, wherein the trained machine learning model is trained to differentiate between a presence or an absence of advanced adenoma and a presence or an absence of benign polyp; and
   responsive to detecting the increased risk of the colorectal cancer, treating the subject with a surgery, a chemotherapy, an immunotherapy, or a radiotherapy for the increased risk of the colorectal cancer.

2. The method of claim 1, wherein the pre-determined protein panel comprises FLT3L, CEACAM5, IL-6RA, IL-8, IL-1RT2, TNC, or a combination thereof.

3. The method of claim 1, wherein the pre-determined protein panel comprises FLT3L, CEACAM5, IL-6RA, IL-8, IL-1RT2, TNC, MUC-16, EGF, or a combination thereof.

4. The method of claim 1, wherein the pre-determined protein panel comprises FLT3L, CEACAM5, and IL-6RA.

5. The method of claim 1, wherein the pre-determined protein panel comprises FLT3L, CEACAM5, IL-6RA, CEA, IL-8, AGP, IL-1RT2, TNC, and GDF-15.

6. The method of claim 1, wherein the pre-determined protein panel comprises FLT3L, CEACAM5, IL-6RA, CEA, IL-8, AGP, IL-1RT2, TNC, GDF-15, AGRP, Haptoglobin, ANGPTL4, FGF-23, Complement component C2, ORM2, FGF-23, MUC-16, EGF, p00738, HE4, or a combination thereof.

7. The method of claim 1, wherein the pre-determined protein panel comprises FLT3L, CEACAM5, IL-6RA, IL-8, IL-1RT2, and TNC.

8. The method of claim 1, wherein the pre-determined protein panel comprises FLT3L, CEACAM5, IL-6RA, ORM, IL-8, AGP, IL-1RT2, TNC, GDF-15, AGRP, Haptoglobin, ANGPTL4, FGF-23, Complement component C2, ORM2, FGF-23, MUC-16, and EGF.

9. The method of claim 1, wherein the pre-determined protein panel comprises total PSA.

10. The method of claim 1, wherein the colorectal cancer is selected from the group consisting of: Lynch syndrome, colon cancer, rectal cancer, colorectal carcinoma, colorectal adenocarcinoma, carcinoid tumors, gastrointestinal carcinoid tumors, gastrointestinal stromal tumors (GIST), lymphomas, and sarcoma.

11. The method of claim 1, wherein the biological sample is selected from the group consisting of: a bodily fluid, stool, colonic effluent, urine, blood plasma, blood serum, whole blood, isolated blood cells, cells isolated from the blood, tissue biopsy, and a combination thereof.

12. The method of claim 1, wherein the trained machine learning model is trained using a deep learning algorithm, a linear regression, a logistic regression, a support vector machine (SVM), a neural network, or a Random Forest.

13. The method of claim 1, wherein the computer is programmed with instructions to further stratify the colorectal cancer of the subject, at least in part by using the trained machine learning model to determine a sub-type of the colorectal cancer of the subject from among a plurality of distinct sub-types or stages of colorectal cancer.

14. A method of detecting a cancer in a subject, wherein the cancer comprises a colorectal cancer, the method comprising:
(a) obtaining a protein profile of the subject comprising a measured amount of a protein from a pre-determined protein panel comprising at least three proteins selected from the group consisting of: epidermal growth factor (EGF), fibroblast growth factor 2 (FGF-2), FMS-like tyrosine kinase 3 ligand (FLT3L), Fractalkine, Interleukin-1 alpha (IL-1a), IL-2, IL-6, IL-8, GRO-alpha-MGSA (GROa), Macrophage inflammatory protein-3 alpha (MIP-3a), Complement component C2, Complement component C9, Factor D, Factor I, Mannose-binding lectin (MBL), matrix metalloproteinase-2 (MMP-2), Growth/Differentiation Factor-15 (GDF-15), Osteonectin, Periostin, Angiopoietin-like 4 (ANGPTL4), FGF-21, FGF-23, hepatocyte growth factor (HGF), Angiopoietin-2, Bone Morphogenetic Protein-9 (BMP-9), IL-1RII, hepatocyte growth factor receptor (HGFR), IL-6ra, Osteopontin (OPN), Tenascin-C, Thrombospondin-2, urokinase plasminogen activator surface receptor (uPAR), CD44, Kallikrein-6, Mesothelin, epithelial cellular adhesion molecule (EpCAM), Apo A1, alpha-1-acid glycoprotein (AGP), Alpha-2-macroglobulin (A2MB), Fetuin A, haptoglobin (HP), L-Selectin, Complement component C1q, Complement component C3, Complement component C3b, Factor B, Factor H, Properdin, Agouti-Related Protein (AGRP), MMP-12, Cytokeratin-19 fragment 21-1 (CYFRA21-1), Human epididymis protein 4 (HE4), total prostate-specific antigen (PSA), Macrophage migration inhibitory factor (MIF), alpha fetoprotein (AFP), cancer antigen 125 (CA125), CA19-9, CA15-3 (MUC-1), and carcinoembryonic antigen (CEA), in a biological sample obtained or derived from the subject;
(b) detecting an increased risk of the colorectal cancer in the subject, wherein the detecting comprises processing the protein profile using a trained machine learning model, wherein the trained machine learning model is trained with training data comprising: (i) a first set of biological samples obtained or derived from subjects with advanced adenoma, (ii) a second set of biological samples obtained or derived from control subjects without advanced adenoma, (iii) a third set of biological samples obtained or derived from subjects with benign polyp, and (iv) a fourth set of biological samples obtained or derived from control subjects without benign polyp, to provide an output value indicative of the increased risk of the colorectal cancer, wherein the trained machine learning model is trained to differentiate between a presence or an absence of advanced adenoma and a presence or an absence of benign polyp; and
(c) responsive to detecting the increased risk of the colorectal cancer, treating the subject with a surgery, a chemotherapy, an immunotherapy, or a radiotherapy for the increased risk of the colorectal cancer.

15. The method of claim 1, further comprising assaying the biological sample obtained or derived from the subject to obtain the protein profile of the subject.

16. The method of claim 11, wherein the biological sample obtained or derived from the subject comprises the blood plasma.

17. The method of claim 1, wherein the pre-determined protein panel comprises at least six proteins selected from the group consisting of: epidermal growth factor (EGF), fibroblast growth factor 2 (FGF-2), FMS-like tyrosine kinase 3 ligand (FLT3L), Fractalkine, Interleukin-1 alpha (IL-1a), IL-2, IL-6, IL-8, GRO-alpha-MGSA (GROa), Macrophage inflammatory protein-3 alpha (MIP-3a), Complement component C2, Complement component C9, Factor D, Factor I, Mannose-binding lectin (MBL), matrix metalloproteinase-2 (MMP-2), Growth/Differentiation Factor-15 (GDF-15), Osteonectin, Periostin, Angiopoietin-like 4 (ANGPTL4), FGF-21, FGF-23, hepatocyte growth factor (HGF), Angiopoietin-2, Bone Morphogenetic Protein-9 (BMP-9), IL-1RII, hepatocyte growth factor receptor (HGFR), IL-6ra, Osteopontin (OPN), Tenascin-C, Thrombospondin-2, urokinase plasminogen activator surface receptor (uPAR), CD44, Kallikrein-6, Mesothelin, epithelial cellular adhesion molecule (EpCAM), Apo A1, alpha-1-acid glycoprotein (AGP), Alpha-2-macroglobulin (A2MB), Fetuin A, haptoglobin (HP), L-Selectin, Complement component C1q, Complement component C3, Complement component C3b, Factor B, Factor H, Properdin, Agouti-Related Protein (AGRP), MMP-12, Cytokeratin-19 fragment 21-1 (CYFRA21-1), Human epididymis protein 4 (HE4), total prostate-specific antigen (PSA), Macrophage migration inhibitory factor (MIF), alpha fetoprotein (AFP), cancer antigen 125 (CA125), CA19-9, CA15-3 (MUC-1), and carcinoembryonic antigen (CEA).

18. The method of claim 1, wherein the training data further comprises: (iii) a fifth set of biological samples obtained or derived from subjects with colorectal cancer, and (iv) a sixth set of biological samples obtained or derived from control subjects without colorectal cancer.

19. The method of claim 1, further comprising performing a colonoscopy on the subject to detect the colorectal cancer.

20. The method of claim 14, further comprising performing a colonoscopy on the subject to detect the colorectal cancer.

* * * * *